(12) United States Patent
Lee et al.

(10) Patent No.: US 11,299,559 B2
(45) Date of Patent: Apr. 12, 2022

(54) MODIFIED CONJUGATED DIENE-BASED POLYMER AND RUBBER COMPOSITION INCLUDING THE SAME

(71) Applicant: LG Chem, Ltd., Seoul (KR)

(72) Inventors: Ho Young Lee, Daejeon (KR); Jae Hoon Choe, Daejeon (KR); Kyung Chang Seo, Daejeon (KR); No Ma Kim, Daejeon (KR)

(73) Assignee: LG Chem, Ltd.

( * ) Notice: Subject to any disclaimer, the term of this patent is extended or adjusted under 35 U.S.C. 154(b) by 0 days.

(21) Appl. No.: 16/754,600

(22) PCT Filed: Nov. 30, 2018

(86) PCT No.: PCT/KR2018/015143
§ 371 (c)(1),
(2) Date: Apr. 8, 2020

(87) PCT Pub. No.: WO2019/112261
PCT Pub. Date: Jun. 13, 2019

(65) Prior Publication Data
US 2020/0354482 A1 Nov. 12, 2020

(30) Foreign Application Priority Data

Dec. 5, 2017 (KR) .................. 10-2017-0165578
Nov. 29, 2018 (KR) .................. 10-2018-0150918

(51) Int. Cl.
*C08C 19/28* (2006.01)
*C07C 211/27* (2006.01)
*C07D 295/03* (2006.01)
*C07D 295/033* (2006.01)
*C08F 236/10* (2006.01)
*C08K 3/36* (2006.01)
*B60C 1/00* (2006.01)

(52) U.S. Cl.
CPC ............ *C08C 19/28* (2013.01); *C07C 211/27* (2013.01); *C07D 295/03* (2013.01); *C07D 295/033* (2013.01); *C08F 236/10* (2013.01); *C08K 3/36* (2013.01); *B60C 1/00* (2013.01)

(58) Field of Classification Search
CPC . C07C 211/27; C07D 295/03; C07D 295/033; C08K 3/36; B60C 1/00
See application file for complete search history.

(56) References Cited

U.S. PATENT DOCUMENTS

| | | | |
|---|---|---|---|
| 4,397,994 A | 8/1983 | Takeuchi et al. | |
| 2004/0254301 A1 | 12/2004 | Tsukimawashi et al. | |
| 2008/0033110 A1* | 2/2008 | Suzuki | C08F 4/10 525/185 |
| 2009/0111933 A1 | 4/2009 | Yamada et al. | |
| 2013/0023624 A1 | 1/2013 | Sekikawa et al. | |
| 2014/0213721 A1* | 7/2014 | Yamada | C08K 3/36 524/572 |
| 2014/0371383 A1 | 12/2014 | Hayata et al. | |
| 2016/0053059 A1 | 2/2016 | Kim et al. | |
| 2016/0208024 A1* | 7/2016 | Kim | C08F 236/10 |
| 2016/0347877 A1* | 12/2016 | Lee | C08F 236/10 |
| 2016/0355612 A1 | 12/2016 | Chun et al. | |
| 2017/0022298 A1* | 1/2017 | Sohn | C07F 7/1804 |
| 2017/0369599 A1 | 12/2017 | Tajima | |
| 2018/0037674 A1* | 2/2018 | Yamada | C08C 19/25 |
| 2018/0127333 A1* | 5/2018 | Lee | B01J 31/2295 |
| 2018/0201699 A1* | 7/2018 | Lee | B60C 1/00 |
| 2018/0208684 A1* | 7/2018 | Choe | C08F 2/44 |
| 2018/0223006 A1* | 8/2018 | Lee | C08K 5/5415 |
| 2018/0258194 A1* | 9/2018 | Sohn | C08C 19/22 |
| 2019/0085099 A1* | 3/2019 | Kim | C08F 8/30 |
| 2020/0277426 A1* | 9/2020 | Oh | C08F 8/42 |

FOREIGN PATENT DOCUMENTS

| | | | |
|---|---|---|---|
| CN | 103980390 A | | 8/2014 |
| JP | H06271706 A | | 9/1994 |
| JP | 2003171418 A | | 6/2003 |
| JP | 2006291117 A | * | 10/2006 |
| JP | 2014025031 A | * | 2/2014 |
| JP | 2014136758 A | * | 7/2014 |
| JP | 2017503910 A | | 2/2017 |

(Continued)

OTHER PUBLICATIONS

International Search Report from Application No. PCT/KR2018/015143 dated Mar. 8, 2019, 2 pages.

(Continued)

*Primary Examiner* — Alexander R Pagano
(74) *Attorney, Agent, or Firm* — Lerner, David, Littenberg, Krumholz & Mentlik, LLP

(57) ABSTRACT

A modified conjugated diene-based polymer and a rubber composition including a modified conjugated diene-based polymer are disclosed herein. In some embodiments, a modified conjugated diene-based polymer includes a functional group derived from a modification initiator at one terminal and a functional group derived from a modifier represented by the Formula 2 or Formula 3 at the other terminal, wherein the modified conjugated diene-based polymer having a unimodal molecular weight distribution, and a polydispersity index of 1.0 to less than 1.7. The modified conjugated diene-based polymer prepared by continuous polymerization and having remarkable processability, narrow molecular weight distribution and excellent physical properties.

12 Claims, 3 Drawing Sheets

(56) References Cited

FOREIGN PATENT DOCUMENTS

| KR | 100932356 B1 | 12/2009 |
|----|--------------|---------|
| KR | 20140127716 A | 11/2014 |
| KR | 20150144130 A | 12/2015 |
| KR | 101600722 B1 | 3/2016 |
| KR | 20160062950 A | 6/2016 |
| KR | 20160065733 A | 6/2016 |
| KR | 20170075662 A | 7/2017 |
| KR | 20170098256 A | 8/2017 |
| KR | 20170102320 A | 9/2017 |
| KR | 20170121694 A | 11/2017 |
| WO | 2016133202 A1 | 8/2016 |
| WO | 2017188641 A2 | 11/2017 |

OTHER PUBLICATIONS

Taiwanese Search Report for Application No. 107143237 dated Feb. 16, 2022, 1 page.

* cited by examiner

MODIFIED CONJUGATED DIENE-BASED POLYMER AND RUBBER COMPOSITION INCLUDING THE SAME

CROSS-REFERENCE TO RELATED APPLICATIONS

The present application is a national phase entry under 35 U.S.C. § 371 of International Application No. PCT/KR2018/015143, filed on Nov. 30, 2018, which claims priority from Korean Patent Application Nos. 10-2017-0165578, filed on Dec. 5, 2017, and 10-2018-0150918, filed on Nov. 29, 2018, the entire contents of which are incorporated by reference herein.

TECHNICAL FIELD

The present invention relates to a modified conjugated diene-based polymer having remarkable processability and excellent tensile properties and viscoelasticity properties, and a rubber composition including the same.

BACKGROUND ART

According to the recent demand for cars having a low fuel consumption ratio, a conjugated diene-based polymer having modulational stability represented by wet skid resistance as well as low rolling resistance, and excellent abrasion resistance and tensile properties is required as a rubber material for tires.

In order to reduce the rolling resistance of tires, there is a method of reducing hysteresis loss of vulcanized rubber, and rebound resilience at 50° C. to 80° C., tan δ, Goodrich heating, or the like is used as an evaluation index of the vulcanized rubber. That is, it is desirable to use a rubber material having high rebound resilience at the above temperature or a low tan δ value or Goodrich heating.

Natural rubbers, polyisoprene rubbers, or polybutadiene rubbers are known as rubber materials having low hysteresis loss, but these rubbers have a limitation of low wet skid resistance. Thus, recently, conjugated diene-based polymers or copolymers such as styrene-butadiene rubbers (hereinafter, referred to as "SBR") and butadiene rubbers (hereinafter, referred to as "BR"), are prepared by emulsion polymerization or solution polymerization to be used as rubbers for tires. Among these polymerization methods, the greatest advantage of the solution polymerization in comparison to the emulsion polymerization is that the vinyl structure content and the styrene content, which specify physical properties of the rubber, may be arbitrarily adjusted and its molecular weight and physical properties may be controlled by coupling or modification. Thus, the SBR prepared by the solution polymerization is widely used as a rubber material for tires because it is easy to change a structure of the finally prepared SBR or BR, and movement of chain terminals may be reduced and a coupling force with a filler such as silica and carbon black may be increased by coupling or modification of the chain terminals.

If the solution-polymerized SBR is used as the rubber material for tires, since a glass transition temperature of the rubber is increased by increasing the vinyl content in the SBR, physical properties such as running resistance and braking force, required for tires may be controlled, and fuel consumption may also be reduced by appropriately adjusting the glass transition temperature. The solution-polymerized SBR is prepared by using an anionic polymerization initiator and is being used by coupling or modifying the chain terminals of the polymer thus formed using various modifiers. For example, U.S. Pat. No. 4,397,994 discloses a method of coupling active anions of the chain terminals of a polymer obtained by polymerizing styrene-butadiene using alkyllithium which is a monofunctional initiator in a non-polar solvent, using a binder such as a tin compound.

Meanwhile, the polymerization of the SBR or BR may be performed by batch or continuous polymerization. In case of the batch polymerization, the molecular weight distribution of the polymer thus produced is narrow and the batch polymerization is advantageous considering the improvement of physical properties, but productivity is low and processability is inferior. In case of the continuous polymerization, the polymerization may be performed continuously, and productivity is excellent and improvement of processability is advantageous, but molecular weight distribution is wide and physical properties are inferior. Accordingly, for preparing the SBR or BR, studies for improving productivity, processability and physical properties at the same time are consistently required.

DISCLOSURE OF THE INVENTION

Technical Problem

The present invention is devised to solve the above-mentioned problems of the conventional technique, and an object of the present invention is to provide a modified conjugated diene-based polymer prepared by continuous polymerization and having remarkable processability and excellent physical properties such as tensile properties and viscoelasticity properties, and a rubber composition including the same.

Technical Solution

To solve the above-described tasks, according to an embodiment of the present invention, there is provided a modified conjugated diene-based polymer having a unimodal molecular weight distribution, as indicated by a unimodal shape molecular weight distribution curve obtained by gel permeation chromatography (GPC), and polydispersity index (PDI) of 1.0 to less than 1.7, and including a functional group derived from a modification initiator at one terminal and a functional group derived from a modifier represented by the following Formula 2 or Formula 3 at the other terminal, wherein the modification initiator is a reaction product of a compound represented by the following Formula 1 and an organometal compound:

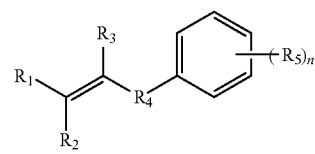

[Formula 1]

in Formula 1, $R_1$ to $R_3$ are each independently hydrogen; an alkyl group of 1 to 30 carbon atoms; an alkenyl group of 2 to 30 carbon atoms; an alkynyl group of 2 to 30 carbon atoms; a heteroalkyl group of 1 to 30 carbon atoms, a heteroalkenyl group of 2 to 30 carbon atoms; a heteroalkynyl group of 2 to 30 carbon atoms; a cycloalkyl group of 5 to 30 carbon atoms; an aryl group of 6 to 30 carbon atoms; or a heterocyclic group of 3 to 30 carbon atoms, $R_4$ is a single bond; a substituted or unsubstituted alkylene group of 1 to 20 carbon atoms with a substituent; a substituted or unsubstituted cycloalkylene group of 5 to 20 carbon atoms with a substituent; or a substituted or unsubstituted arylene group of 6 to 20 carbon atoms with a substituent, wherein the substituent is an alkyl group of 1 to 10 carbon atoms, a cycloalkyl group of 5 to 10 carbon atoms, or an aryl group of 6 to 20 carbon atoms, $R_5$ is an alkyl group of 1 to 30 carbon atoms; an alkenyl group of 2 to 30 carbon atoms; an alkynyl group of 2 to 30 carbon atoms; a heteroalkyl group of 1 to 30 carbon atoms; a heteroalkenyl group of 2 to 30 carbon atoms; a heteroalkynyl group of 2 to 30 carbon atoms; a cycloalkyl group of 5 to 30 carbon atoms; an aryl group of 6 to 30 carbon atoms; a heterocyclic group of 3 to 30 carbon atoms; or a functional group represented by the following Formula 1a or Formula 1b, and n is an integer of 1 to 5, and at least one of $R_5$ groups is a functional group represented by the following Formula 1a or Formula 1b, in case where n is an integer of 2 to 5, a plurality of $R_5$ groups may be the same or different,

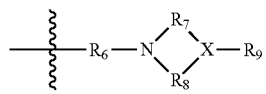

[Formula 1a]

in Formula 1a, $R_6$ is a substituted or unsubstituted alkylene group of 1 to 20 carbon atoms with a substituent; a substituted or unsubstituted cycloalkylene group of 5 to 20 carbon atoms with a substituent; or a substituted or unsubstituted arylene group of 6 to 20 carbon atoms with a substituent, wherein the substituent is an alkyl group of 1 to 10 carbon atoms, a cycloalkyl group of 5 to 10 carbon atoms, or an aryl group of 6 to 20 carbon atoms, $R_7$ and $R_8$ are each independently a substituted or unsubstituted alkylene group of 1 to 20 carbon atoms with alkyl group of 1 to 10 carbon atoms, a cycloalkyl group of 5 to 10 carbon atoms, or aryl group of 6 to 20 carbon atoms, $R_9$ is hydrogen; an alkyl group of 1 to 30 carbon atoms, an alkenyl group of 2 to 30 carbon atoms; an alkynyl group of 2 to 30 carbon atoms; a heteroalkyl group of 1 to 30 carbon atoms; a heteroalkenyl group of 2 to 30 carbon atoms; a heteroalkynyl group of 2 to 30 carbon atoms; a cycloalkyl group of 5 to 30 carbon atoms; an aryl group of 6 to 30 carbon atoms; or a heterocyclic group of 3 to 30 carbon atoms, and X is an N, O or S atom, in case where X is O or S, $R_9$ is not present,

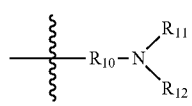

[Formula 1b]

in Formula 1b, $R_{10}$ is a substituted or unsubstituted alkylene group of 1 to 20 carbon atoms with a substituent; a substituted or unsubstituted cycloalkylene group of 5 to 20 carbon atoms with a substituent; or a substituted or unsubstituted arylene group of 6 to 20 carbon atoms with a substituent, wherein the substituent is an alkyl group of 1 to 10 carbon atoms, a cycloalkyl group of 5 to 10 carbon atoms, or an aryl group of 6 to 20 carbon atoms, and $R_{11}$ and $R_{12}$ are each independently an alkyl group of 1 to 30 carbon atoms; an alkenyl group of 2 to 30 carbon atoms; an alkynyl group of 2 to 30 carbon atoms; a heteroalkyl group of 1 to 30 carbon atoms; a heteroalkenyl group of 2 to 30 carbon atoms; a heteroalkynyl group of 2 to 30 carbon atoms; a cycloalkyl group of 5 to 30 carbon atoms; an aryl group of 6 to 30 carbon atoms; or a heterocyclic group of 3 to 30 carbon atoms,

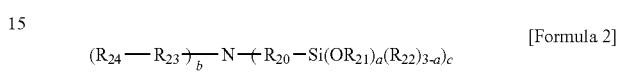

[Formula 2]

in Formula 2, $R_{20}$ is a single bond, or an alkylene group of 1 to 10 carbon atoms, $R_{21}$ and $R_{22}$ are each independently an alkyl group of 1 to 10 carbon atoms, $R_{23}$ is a single bond or an alkylene group of 1 to 10 carbon atoms, $R_{24}$ is hydrogen, an alkyl group of 1 to 10 carbon atoms or a substituted divalent, trivalent or tetravalent alkylsilyl group with an alkyl group of 1 to 10 carbon atoms, a is an integer of 2 or 3, c is an integer of 1 to 3, and b is an integer of 0 to 2, where b+c=3,

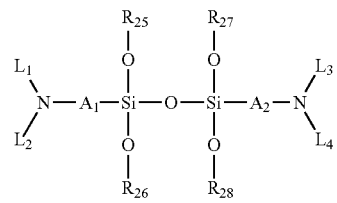

[Formula 3]

in Formula 3, $A_1$ and $A_2$ are each independently an alkylene group of 1 to 20 carbon atoms, $R_{25}$ to $R_{28}$ are each independently an alkyl group of 1 to 20 carbon atoms, and $L_1$ to $L_4$ are each independently a substituted divalent, trivalent or tetravalent alkylsilyl group with an alkyl group of 1 to 10 carbon atoms, or an alkyl group of 1 to 20 carbon atoms.

In addition, the present invention provides a rubber composition including the modified conjugated diene-based polymer and a filler.

Advantageous Effects

The modified conjugated diene-based polymer according to the present invention is prepared by continuous polymerization which will be described later, and has a unimodal molecular weight distribution and narrow molecular weight distribution as defined by a polydispersity index of less than 1.7, and thus, has excellent processability, tensile properties and viscoelasticity properties.

In addition, the modified conjugated diene-based polymer according to the present invention includes a functional group derived from a modification initiator at one terminal and a functional group derived from a modifier at the other terminal, thereby showing further improved viscoelasticity properties.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

BEST MODE FOR CARRYING OUT THE INVENTION

Figure 1:
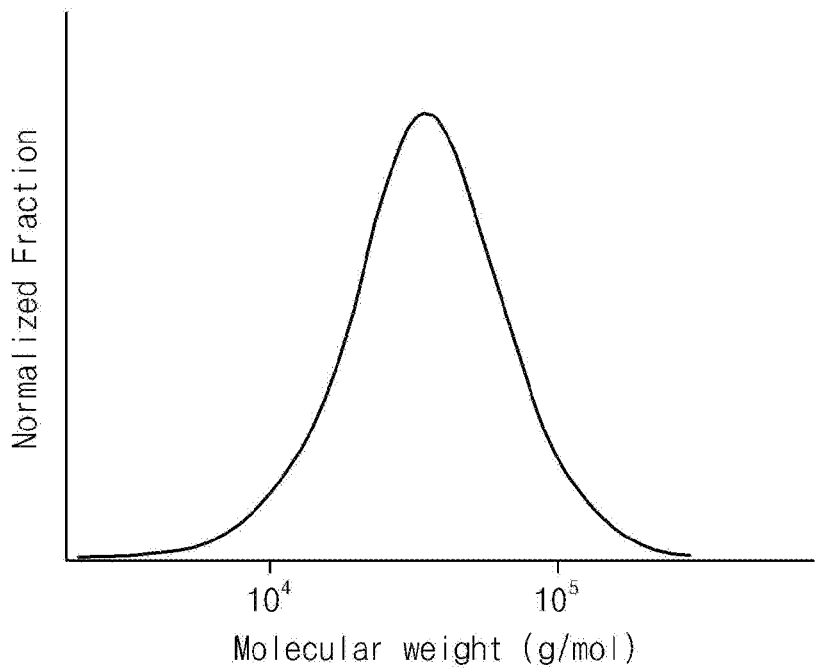
FIG. 1 shows a molecular weight distribution curve by gel permeation chromatography (GPC) of a modified conjugated diene-based polymer of Example 1 according to an embodiment of the present invention.
Figure 2:
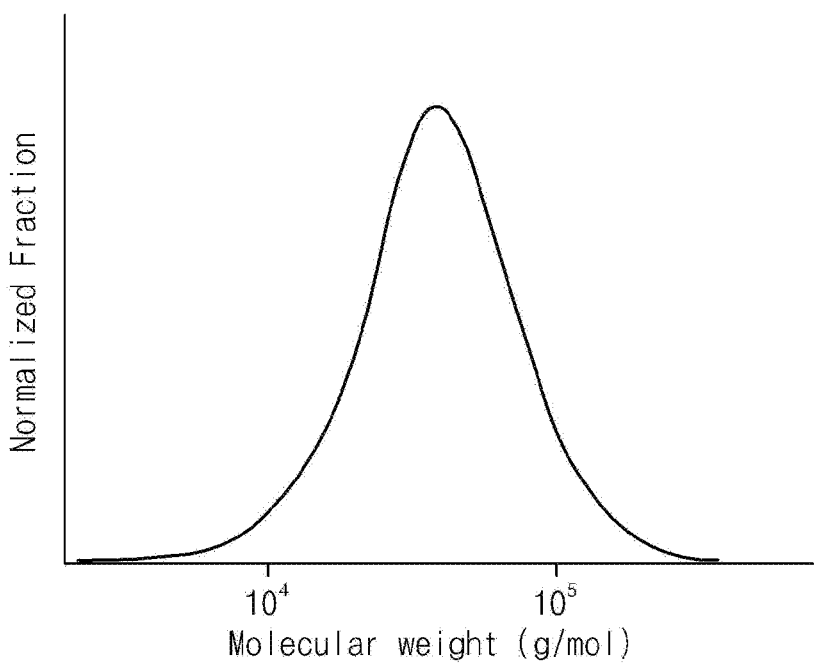
FIG. 2 shows a molecular weight distribution curve by gel permeation chromatography (GPC) of a modified conjugated diene-based polymer of Example 5 according to an embodiment of the present invention.

Hereinafter, the present invention will be described in more detail in order to assist the understanding of the present invention.

It will be understood that words or terms used in the description and claims of the present invention shall not be interpreted as the meaning defined in commonly used dictionaries. It will be further understood that the words or terms should be interpreted as having a meaning that is consistent with their meaning of the technical idea of the invention, based on the principle that an inventor may properly define the meaning of the words or terms to best explain the invention.

The term "alkyl group" used in the present invention may mean monovalent aliphatic saturated hydrocarbon, and may include both a linear alkyl group such as methyl, ethyl, propyl and butyl, and a branched alkyl group such as isopropyl, sec-butyl, tert-butyl and neo-pentyl.

The term "alkylene group" used in the present invention may mean divalent aliphatic saturated hydrocarbon such as methylene, ethylene, propylene and butylene.

The term "alkenyl group" used in the present invention may mean monovalent aliphatic unsaturated hydrocarbon including one or two or more double bonds.

The term "alkynyl group" used in the present invention may mean monovalent aliphatic unsaturated hydrocarbon including one or two or more triple bonds.

The term "cycloalkyl group" used in the present invention may mean cyclic saturated hydrocarbon.

The term "aryl group" used in the present invention may mean cyclic aromatic hydrocarbon, and may include both monocyclic aromatic hydrocarbon including one ring, and polycyclic aromatic hydrocarbon including two or more bonded rings.

The term "heteroalkyl group" used in the present invention may mean an alkyl group in which a carbon atom (excluding a terminal carbon atom) in the alkyl group is substituted with one or more heteroatoms, where the heteroatom may be selected from N, O and S.

The term "heteroalkenyl group" used in the present invention may mean an alkenyl group in which a carbon atom (excluding a terminal carbon atom) in the alkenyl group is substituted with one or more heteroatoms, where the heteroatom may be selected from N, O and S.

The term "heteroalkynyl group" used in the present invention may mean an alkynyl group in which a carbon atom (excluding a terminal carbon atom) in the alkynyl group is substituted with one or more heteroatoms, where the heteroatom may be selected from N, O and S.

The term "heterocyclic group" used in the present invention may mean a cycloalkyl group in which a carbon atom in cyclic saturated hydrocarbon or cyclic unsaturated hydrocarbon including one or more unsaturated bonds, is substituted with one or more heteroatoms, where the heteroatom may be selected from N, O and S.

The term "derived unit" and "derived functional group" used in the present invention may represent a component or a structure comes from a certain material, or the material itself.

The term "single bond" used in the present invention may mean a single covalent bond itself, not including a separate atomic or molecular group.

The present invention provides a modified conjugated diene-based polymer prepared by continuous polymerization and having remarkable processability, narrow molecular weight distribution and excellent physical properties.

The modified conjugated diene-based polymer according to an embodiment of the present invention has a unimodal molecular weight distribution, as indicated by a unimodal shape molecular weight distribution curve obtained by gel permeation chromatography (GPC), and polydispersity index (PDI) of 1.0 to less than 1.7, and includes a functional group derived from a modification initiator at one terminal and a functional group derived from a modifier represented by the following Formula 2 or Formula 3 at the other terminal, wherein the modification initiator is a reaction product of a compound represented by the following Formula 1 and an organometal compound:

[Formula 1]

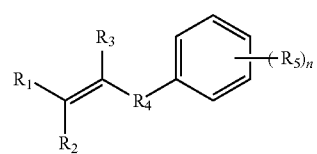

in Formula 1, $R_1$ to $R_3$ are each independently hydrogen; an alkyl group of 1 to 30 carbon atoms, an alkenyl group of 2 to 30 carbon atoms; an alkynyl group of 2 to 30 carbon atoms; a heteroalkyl group of 1 to 30 carbon atoms, a heteroalkenyl group of 2 to 30 carbon atoms; a heteroalkynyl group of 2 to 30 carbon atoms; a cycloalkyl group of 5 to 30 carbon atoms; an aryl group of 6 to 30 carbon atoms; or a heterocyclic group of 3 to 30 carbon atoms, $R_4$ is a single bond; a substituted or unsubstituted alkylene group of 1 to carbon atoms with a substituent; a substituted or unsubstituted cycloalkylene group of 5 to 20 carbon atoms with a substituent; or a substituted or unsubstituted arylene group of 6 to 20 carbon atoms with a substituent, wherein the substituent is an alkyl group of 1 to 10 carbon atoms, a cycloalkyl group of 5 to 10 carbon atoms, or an aryl group of 6 to 20 carbon atoms, $R_5$ is an alkyl group of 1 to 30 carbon atoms; an alkenyl group of 2 to 30 carbon atoms; an alkynyl group of 2 to 30 carbon atoms; a heteroalkyl group of 1 to 30 carbon atoms; a heteroalkenyl group of 2 to 30 carbon atoms; a heteroalkynyl group of 2 to 30 carbon atoms; a cycloalkyl group of 5 to 30 carbon atoms; an aryl group of 6 to 30 carbon atoms; a heterocyclic group of 3 to 30 carbon atoms; or a functional group represented by the following Formula 1a or Formula 1b, n is an integer of 1 to 5, and at least one of $R_5$ groups is a functional group represented by the following Formula 1a or Formula 1b, where in case where n is an integer of 2 to 5, a plurality of $R_5$ groups may be the same or different,

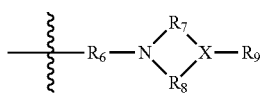

[Formula 1a]

in Formula 1a, $R_6$ is a substituted or unsubstituted alkylene group of 1 to 20 carbon atoms with a substituent; a substituted or unsubstituted cycloalkylene group of 5 to 20 carbon atoms with a substituent; or a substituted or unsubstituted arylene group of 6 to 20 carbon atoms with a substituent, wherein the substituent is an alkyl group of 1 to 10 carbon atoms, a cycloalkyl group of 5 to 10 carbon atoms, or an aryl group of 6 to 20 carbon atoms, $R_7$ and $R_8$ are each independently a substituted or unsubstituted alkylene group of 1 to 20 carbon atoms with an alkyl group of 1 to 10 carbon atoms, a cycloalkyl group of 5 to 10 carbon atoms, or an aryl group of 6 to 20 carbon atoms, $R_9$ is hydrogen; an alkyl group of 1 to 30 carbon atoms; an alkenyl group of 2 to 30 carbon atoms; an alkynyl group of 2 to 30 carbon atoms; a heteroalkyl group of 1 to 30 carbon atoms; a heteroalkenyl group of 2 to 30 carbon atoms; a heteroalkynyl group of 2 to 30 carbon atoms; a cycloalkyl group of 5 to 30 carbon atoms; an aryl group of 6 to 30 carbon atoms; or a heterocyclic group of 3 to 30 carbon atoms, and X is an N, O or S atom, in case where X is O or S, $R_9$ is not present,

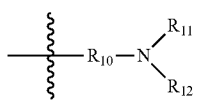

[Formula 1b]

in Formula 1b, $R_{10}$ is a substituted or unsubstituted alkylene group of 1 to 20 carbon atoms with a substituent; a substituted or unsubstituted cycloalkylene group of 5 to 20 carbon atoms with a substituent; or a substituted or unsubstituted arylene group of 6 to 20 carbon atoms with a substituent, wherein the substituent is an alkyl group of 1 to 10 carbon atoms, a cycloalkyl group of 5 to 10 carbon atoms, or an aryl group of 6 to 20 carbon atoms, and $R_{11}$ and $R_{12}$ are each independently an alkyl group of 1 to 30 carbon atoms; an alkenyl group of 2 to 30 carbon atoms; an alkynyl group of 2 to 30 carbon atoms; a heteroalkyl group of 1 to 30 carbon atoms; a heteroalkenyl group of 2 to 30 carbon atoms; a heteroalkynyl group of 2 to 30 carbon atoms; a cycloalkyl group of 5 to 30 carbon atoms; an aryl group of 6 to 30 carbon atoms; or a heterocyclic group of 3 to 30 carbon atoms,

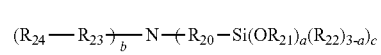

[Formula 2]

in Formula 2, $R_{20}$ is a single bond, or an alkylene group of 1 to 10 carbon atoms, $R_{21}$ and $R_{22}$ are each independently an alkyl group of 1 to 10 carbon atoms, $R_{23}$ is a single bond or an alkylene group of 1 to 10 carbon atoms, $R_{24}$ is hydrogen, an alkyl group of 1 to 10 carbon atoms or a substituted divalent, trivalent or tetravalent alkylsilyl group with an alkyl group of 1 to 10 carbon atoms, a is an integer of 2 or 3, c is an integer of 1 to 3, and b is an integer of 0 to 2, where b+c=3,

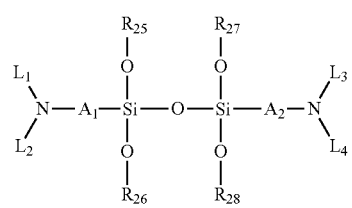

[Formula 3]

in Formula 3, $A_1$ and $A_2$ are each independently an alkylene group of 1 to 20 carbon atoms, $R_{25}$ to $R_{28}$ are each independently an alkyl group of 1 to 20 carbon atoms, and $L_1$ to $L_4$ are each independently a substituted divalent, trivalent or tetravalent alkylsilyl group with an alkyl group of 1 to 10 carbon atoms, or an alkyl group of 1 to 20 carbon atoms.

According to an embodiment of the present invention, the modified conjugated diene-based polymer may include a repeating unit derived from a conjugated diene-based monomer, a functional group derived from a modification initiator and a functional group derived from a modifier. The repeating unit derived from a conjugated diene-based monomer may mean a repeating unit formed by a conjugated diene-based monomer during polymerization, and the functional group derived from a modification initiator and the functional group derived from a modifier may mean functional groups derived from a modification initiator and a modifier, which are present at the terminals of a polymer chain, respectively.

In addition, according to another embodiment of the present invention, the modified conjugated diene-based polymer may be a copolymer including a repeating unit derived from a conjugated diene-based monomer, a repeating unit derived from an aromatic vinyl monomer, a functional group derived from a modification initiator and a functional group derived from a modifier. Here, the repeating unit derived from an aromatic vinyl monomer may mean a repeating unit formed by an aromatic vinyl monomer during polymerization.

According to an embodiment of the present invention, the conjugated diene-based monomer may be one or more selected from the group consisting of 1,3-butadiene, 2,3-dimethyl-1,3-butadiene, piperylene, 3-butyl-1,3-octadiene, isoprene, 2-phenyl-1,3-butadiene, and 2-halo-1,3-butadiene (halo means a halogen atom).

The aromatic vinyl monomer may include, for example, one or more selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, 1-vinyl-5-hexylnaphthalene, 3-(2-pyrrolidino ethyl)styrene, 4-(2-pyrrolidino ethyl)styrene, and 3-(2-pyrrolidino-1-methyl ethyl)-α-methylstyrene.

In another embodiment, the modified conjugated diene-based polymer may be a copolymer further including a repeating unit derived from a diene-based monomer of 1 to 10 carbon atoms together with the repeating unit derived from a conjugated diene-based monomer. The repeating unit derived from a diene-based monomer may be a repeating unit derived from a diene-based monomer different from the conjugated diene-based monomer, and the diene-based monomer different from the conjugated diene-based monomer may be, for example, 1,2-butadiene. If the modified conjugated diene-based polymer is a copolymer further including a diene-based monomer, the modified conjugated diene-based polymer may include the repeating unit derived from the diene-based monomer in greater than 0 wt % to 1 wt %, greater than 0 wt % to 0.1 wt %, greater than 0 wt % to 0.01 wt %, or greater than 0 wt % to 0.001 wt %, and within this range, preventing effect of gel formation may be achieved.

According to an embodiment of the present invention, the copolymer may be a random copolymer, and in this case, effect of excellent balance among each of physical properties may be achieved. The random copolymer may mean the repeating units constituting a copolymer arranged in disorder.

The modified conjugated diene-based polymer according to an embodiment of the present invention may have a number average molecular weight (Mn) of 1,000 g/mol to 2,000,000 g/mol, 10,000 g/mol to 1,000,000 g/mol, or 100,000 g/mol to 800,000 g/mol, a weight average molecular weight (Mw) of 1,000 g/mol to 3,000,000 g/mol, 10,000 g/mol to 2,000,000 g/mol, or 100,000 g/mol to 2,000,000 g/mol, and a maximum peak molecular weight (Mp) of 1,000 g/mol to 3,000,000 g/mol, 10,000 g/mol to 2,000,000 g/mol, or 100,000 g/mol to 2,000,000 g/mol. Within these ranges, rolling resistance and wet skid resistance are excellent. In another embodiment, the modified conjugated diene-based polymer may have polydispersity index (PDI; Mw/Mn) of less than 1.7, 1.0 to less than 1.7, or 1.1 to less than 1.7, and within this range, tensile properties and viscoelasticity properties are excellent and balance among physical properties is excellent.

At the same time, the modified conjugated diene-based polymer may have a unimodal molecular weight distribution, as indicated by a unimodal shape molecular weight distribution curve obtained by gel permeation chromatography (GPC). This molecular weight distribution is shown by a polymer polymerized by continuous polymerization, and it means that the modified conjugated diene-based polymer has uniform properties. That is, the modified conjugated diene-based polymer according to an embodiment of the present invention is prepared by continuous polymerization, and may have a unimodal molecular weight distribution and polydispersity index of less than 1.7.

Generally, the molecular weight distribution curve of a conjugated diene-based polymer prepared by preparing a conjugated diene-based polymer by a batch polymerization method and then performing modification reaction is a molecular weight distribution curve of multimodal, i.e., bimodal or more. Particularly, in the batch polymerization, polymerization reaction is initiated after injecting all raw materials, and from an initiation point when polymerization is carried out by a plurality of initiators, the propagation of chains may take place simultaneously. Accordingly, the propagation of each chain may be generally uniform, the molecular weight of the polymer chains thus prepared may be constant, and molecular weight distribution may be significantly narrow to show a unimodal shape. However, in case where a modifier is injected and modification reaction is carried out, two cases of a "unmodified case" and a "modified and coupled case" may occur, two groups having large molecular weight difference may be formed among the polymer chains, and at last, a multimodal molecular weight distribution curve having two or more peaks of a molecular weight distribution curve may be formed. Meanwhile, in the continuous polymerization method according to an embodiment of the present invention, different from the batch polymerization, an initiator and raw materials are continuously injected, initiation points when polymerization is initiated are different, and polymerization is initiated at diverse points including the initiation of the reaction, the intermediate of the reaction, and the terminal of the reaction. Accordingly, after finishing the polymerization reaction, polymer chains with diverse molecular weights are produced. Accordingly, in a curve showing molecular weight distribution, no dominant peak is shown but a wide molecular weight distribution curve is shown as a single peak. In addition, though the coupling of a chain of which polymerization is initiated at the terminal of the reaction is carried out, the molecular weight may be similar to a chain of which polymerization is initiated at the beginning of the reaction, and the diversity of the molecular weight distribution may be kept the same and the unimodal distribution curve may be still kept in general.

However, modification conditions may be controlled to show a unimodal shape though a polymer is polymerized by a batch polymerization method and then modified. However, in this case, the whole polymer is required not to be coupled, or the whole polymer is required to be coupled. Otherwise, a unimodal molecular weight distribution curve may not be shown.

In addition, as described above, in case where the molecular weight distribution curve of the modified conjugated diene-based polymer shows unimodal distribution though prepared by a batch polymerization method and all of the polymer is coupled, polymers having equivalent level of molecular weights are present and thus, processability may be inferior, and functional groups which may interact with a filler such as silica and carbon black decrease due to the coupling, and compounding properties may be inferior. On the contrary, in case where all of the polymer is not coupled, functional groups at the terminal of the polymer, which are required to interact with a filler such as silica and carbon black during processing, predominantly make interaction between the terminal functional groups of the polymer rather than the filler, and the interaction with the filler may be prohibited. Accordingly, processability may become significantly deteriorated, and at last, in case where a polymer is controlled to show a unimodal molecular weight distribution curve while being prepared by the batch polymerization method, the processability and compounding properties of the modified conjugated diene-based polymer thus prepared may be degraded, and particularly, the processability may be markedly degraded.

Meanwhile, the status of the coupling of the modified conjugated diene-based polymer may be checked by coupling number (C.N.), wherein the coupling number is a value dependent on the number of the functional group which is capable of bonding with a polymer present in a modifier after modifying the polymer. That is, the coupling number represents the ratio of a polymer obtained by terminal modification without coupling between polymer chains and a polymer in which a plurality of polymer chains is coupled with one modifier, and may have a range of 1≤C.N.≤F, where F means the number of the functional group in a modifier, which is capable of reacting with the terminal of an active polymer. In other words, a modified conjugated diene-based polymer having the coupling number of 1 means that all polymer chains are not coupled, and a modified conjugated diene-based polymer having the coupling number of F means that all polymer chains are coupled.

Accordingly, the modified conjugated diene-based polymer according to an embodiment of the present invention may have a unimodal shape molecular weight distribution curve and a coupling number greater than 1 and smaller than the number of functional groups of the modifier used (1<C.N.<F).

In another embodiment, the modified conjugated diene-based polymer may have the Si content of 50 ppm or more, 100 ppm or more, 100 ppm to 10,000 ppm, or 100 ppm to 5,000 ppm based on the weight, and within this range, the mechanical properties such as tensile properties and viscoelasticity properties of a rubber composition including the modified conjugated diene-based polymer are excellent. The Si content may mean the amount of Si atoms present in the modified conjugated diene-based polymer. Meanwhile, the Si atom may be derived from the functional group derived from the modifier.

In another embodiment, the modified conjugated diene-based polymer may have the N content of 50 ppm or more, 100 ppm or more, 100 ppm to 10,000 ppm, or 100 ppm to 5,000 ppm based on the total weight, and within this range, the mechanical properties such as tensile properties and viscoelasticity properties of a rubber composition including the modified conjugated diene-based polymer are excellent. The N content may mean the amount of N atoms present in the modified conjugated diene-based polymer, and in this case, the N atom may be derived from the functional group derived from the modifier.

The Si content may be measured via, for example, an inductively coupled plasma (ICP) analysis method, and the ICP analysis method may be measured using an inductively coupled plasma optical emission spectroscopy (ICP-OES; Optima 7300DV). If the inductively coupled plasma optical emission spectroscopy is used, measurement may be performed by adding about 0.7 g of a specimen to a platinum (Pt) crucible, adding about 1 ml of concentrated sulfuric acid (98 wt %, electronic grade) thereto, heating at 300° C. for 3 hours, incinerating the specimen in an electrical furnace (Thermo Scientific, Lindberg Blue M) by the following program of steps 1 to 3:

1) step 1: initial temp 0° C., rate (temp/hr) 180° C./hr, temp (holdtime) 180° C. (1 hr),
2) step 2: initial temp 180° C., rate (temp/hr) 85° C./hr, temp (holdtime) 370° C. (2 hr), and
3) step 3: initial temp 370° C., rate (temp/hr) 47° C./hr, temp (holdtime) 510° C. (3 hr), adding 1 ml of concentrated nitric acid (48 wt %) and 20 µl of concentrated hydrofluoric acid (50 wt %) to a residue, sealing the platinum crucible and shaking for 30 minutes or more, adding 1 ml of boric acid to the specimen, storing at 0° C. for 2 hours or more, diluting in 30 ml ultrapure water, and performing incineration.

In addition, the N content may be measured via, for example, an NSX analysis method, and the measurement by the NSX analysis method may be performed using a quantitative analyzer of a trace amount of nitrogen (NSX-2100H). For example, in case where the quantitative analyzer of a trace amount of nitrogen was used, the quantitative analyzer of a trace amount of nitrogen (Auto sampler, Horizontal furnace, PMT & Nitrogen detector) was turned on, carrier gas flowing amounts were set such that Ar was 250 ml/min, $O_2$ was 350 ml/min, and ozonizer was 300 ml/min, heater was set to 800° C., and the analyzer was stood for about 3 hours for stabilization. After the analyzer was stabilized, a calibration curve in calibration ranges of 5 ppm, 10 ppm, 50 ppm, 100 ppm and 500 ppm was made using nitrogen standard (AccuStandard S-22750-01-5 ml), an area corresponding to each concentration was obtained, and a straight line was obtained using the ratio of concentration vs. area. Then, a ceramic boat holding 20 mg of a specimen was put on the auto sampler of the analyzer and measurement was performed to obtain an area. The N content was calculated using the area of the specimen thus obtained and the calibration curve.

In this case, the specimen used in the NSX analysis method is a modified conjugated diene-based polymer specimen obtained by putting in hot water heated with steam and stirring to remove solvents, and removing remaining monomer and modifier therefrom. In addition, if an oil is added to the specimen, the specimen may be a specimen after extracting (removing) the oil therefrom.

In another embodiment, the modified conjugated diene-based polymer may have a mooney stress relaxation ratio measured at 100° C. of 0.7 or more, 0.7 to 3.0, 0.7 to 2.5, or 0.7 to 2.0.

Here, the mooney stress relaxation ratio represents stress change shown as a response to the same amount of strain and may be measured using a mooney viscometer. Particularly, the mooney stress relaxation ratio was obtained as an absolute value by measuring a mooney viscosity using Large Rotor of MV-2000E of Monsanto Co. at a rotor speed of 2±0.02 rpm at 100° C., by standing a polymer at room temperature (23±3° C.) for 30 minutes or more, collecting 27±3 g of the polymer and putting thereof in a die cavity, and then, operating Platen while applying torque, and then, measuring the gradient value of the mooney viscosity change shown while releasing torque.

Meanwhile, the mooney stress relaxation ratio may be used as the index of the branch structure of a corresponding polymer. For example, if polymer having equivalent mooney viscosity are compared, the mooney stress relaxation ratio may decrease with the increase of the degree of branching, and thus, may be used as the index of the degree of branching.

In addition, the modified conjugated diene-based polymer may have a mooney viscosity at 100° C. of 30 or more, to 150, or 40 to 140, and within this range, processability and productivity may be excellent.

In another embodiment, the modified conjugated diene-based polymer may have a shrinking factor (g') which is obtained by measuring a gel permeation chromatography-light scattering method provided with a viscometer of 1.0 or more, particularly, 1.0 to 3.0, more particularly, 1.0 to 1.3.

Here, the shrinking factor (g') obtained by the measurement of the gel permeation chromatography-light scattering method is a ratio of intrinsic viscosity of a polymer having a branch with respect to intrinsic viscosity of linear polymer having the same absolute molecular weight, and may be used as an index of the branch structure of a polymer having a branch, i.e., an index of a ratio occupied by branch. For example, with the decrease of the shrinking factor, the degree of branching of a corresponding polymer tends to increase. Accordingly, if polymers having the equivalent absolute molecular weight are compared, the shrinking factor decreases with the increase of branch, and the shrinking factor may be used as an index of the degree of branching.

In addition, the shrinking factor is obtained by measuring a chromatogram using a gel chromatography-light scattering measurement apparatus provided with a viscometer, and computing based on a solution viscosity and a light scattering method. Particularly, using a GPC-light scattering measurement apparatus provided with a light scattering detector in which two columns filled with a polystyrene-based gel as a filler are connected and a viscometer, an absolute molecular weight and intrinsic viscosity corresponding to each absolute molecular weight are obtained, intrinsic viscosity of a linear polymer corresponding to the absolute molecular weight is computed, and a shrinking factor is obtained as a ratio of the intrinsic viscosity corresponding to each absolute molecular weight. For example, the shrinking factor was obtained as follows. A specimen was injected to a GPC-light scattering measurement apparatus (Viscotek TDAmax, Malvern Co.) provided with a light scattering detector in which two columns filled with a polystyrene-based gel as a filler were connected and a viscometer, and an absolute molecular weight was obtained from the light scattering detector, intrinsic viscosity [ii] with respect to the absolute molecular weight was obtained from the light scattering detector and the viscometer, intrinsic viscosity $[\eta]_0$ of a linear polymer with respect to the absolute molecular weight was computed through Mathematical Formula 2 below, and an average value of the ratio of intrinsic viscosity ($[\eta]/[\eta]_0$) corresponding to each absolute molecular weight was represented as the shrinking factor. In this case, measurement was performed using a mixture solution of tetrahydrofuran and N,N,N',N'-tetramethylethylenediamine (adjusted by mixing 20 ml of N,N,N',N'-tetramethylethylenediamine with 1 L of tetrahydrofuran) as an eluent, and PL Olexix (Agilent Co.) as a column under conditions of an oven temperature of 40° C. and a THF flow rate of 1.0 ml/min. A specimen was prepared by dissolving 15 mg of a polymer in 10 ml of THF.

$$[\eta]_0 = 10^{-3.883} M^{0.771}$$ [Mathematical Formula 2]

In Mathematical Formula 2, M is an absolute molecular weight.

In addition, the modified conjugated diene-based polymer may have the vinyl content of 5 wt % or more, 10 wt % or more, or 10 wt % to 60 wt %. Here, the vinyl content may mean the amount of not 1,4-added but 1,2-added conjugated diene-based monomer with respect to 100 wt % of a conjugated diene-based copolymer composed of a monomer having a vinyl group and an aromatic vinyl monomer.

Meanwhile, the modification initiator according to an embodiment of the present invention is produced by reacting a compound represented by Formula 1 with an organometal compound, and may introduce a functional group into one terminal of the polymer chain thus polymerized at the same time as the initiation of the polymerization.

Particularly, the compound represented by Formula 1 may be Formula 1 in which $R_1$ to $R_3$ are each independently hydrogen; an alkyl group of 1 to 10 carbon atoms, an alkenyl group of 2 to 10 carbon atoms; or an alkynyl group of 2 to 10 carbon atoms, $R_4$ is a single bond; or an unsubstituted alkylene group of 1 to 10 carbon atoms, $R_5$ is an alkyl group of 1 to 10 carbon atoms; an alkenyl group of 2 to 10 carbon atoms; an alkynyl group of 2 to 10 carbon atoms; or a functional group represented by the following Formula 1a or Formula 1b, in Formula 1a, $R_6$ is an unsubstituted alkylene group of 1 to 10 carbon atoms, $R_7$ and $R_8$ are each independently an unsubstituted alkylene group of 1 to 10 carbon atoms, and $R_9$ is an alkyl group of 1 to 10 carbon atoms; a cycloalkyl group of 5 to 20 carbon atoms; an aryl group of 6 to 20 carbon atoms; or a heterocyclic group of 3 to 20 carbon atoms, and in Formula 1b, $R_{10}$ is an unsubstituted alkylene group of 1 to 10 carbon atoms, $R_{11}$ and $R_{12}$ are each independently an alkyl group of 1 to 10 carbon atoms; a cycloalkyl group of 5 to 20 carbon atoms; an aryl group of 6 to 20 carbon atoms; or a heterocyclic group of 3 to 20 carbon atoms.

More particularly, the compound represented by Formula 1 may be a compound represented by the following Formula 1-1 to Formula 1-3:

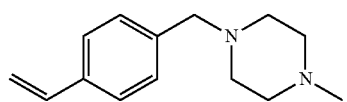

[Formula 1-1]

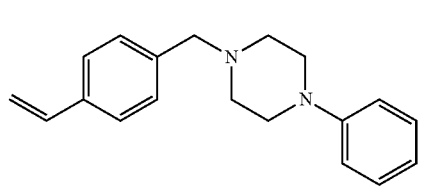

[Formula 1-2]

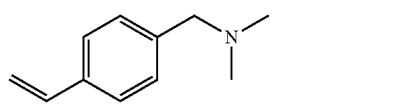

[Formula 1-3]

In addition, the organometal compound may be an organo alkali metal compound, for example, one or more selected from an organolithium compound, an organosodium compound, an organopotassium compound, an organorubidium compound and an organocesium compound.

Particularly, the organometal compound may be one or more selected from methyllithium, ethyllithium, isopropyllithium, n-butyllithium, sec-butyllithium, tert-butyllithium, n-decyllithium, tert-octyllithium, phenyllithium, 1-naphthyllithium, n-eicolithium 4-butylphenyllithium, 4-tolyllithium, cyclohexyllithium, 3,5-di-n-heptylcyclohexyllithium and 4-cyclopentyllithium.

In addition, the modifier according to the present invention may be a modifier for modifying the remaining one terminal of the conjugated diene-based polymer, and in a particular embodiment, may be a modifier having affinity with silica. The modifier having affinity with silica may mean a modifier including a functional group having affinity with silica in a compound used as the modifier, and the functional group having affinity with silica may mean a functional group which has excellent affinity with a filler, particularly a silica-based filler, and is capable of making interaction between a silica-based filler and a functional group derived from a modifier.

Particularly, according to an embodiment of the present invention, the modifier may be a compound represented by Formula 2, and in Formula 2, $R_{20}$ may be a single bond, or an alkylene group of 1 to 5 carbon atoms, $R_{21}$ and $R_{22}$ may be each independently an alkyl group of 1 to 5 carbon atoms, $R_{23}$ may be a single bond or an alkylene group of 1 to 5 carbon atoms, $R_{24}$ may be hydrogen, an alkyl group of 1 to 5 carbon atoms or a substituted tetravalent alkylsilyl group with an alkyl group of 1 to 5 carbon atoms, a may be an integer of 2 or 3, c may be an integer of 1 to 3, and b may be an integer of 0 to 2, where an equation, b+c=3 may be satisfied.

In a more particular embodiment, the compound represented by Formula 2 may be one selected from the group consisting of N,N-bis(3-(dimethoxy(methyl)silyl)propyl)-methyl-1-amine, N,N-bis(3-(diethoxy(methyl)silyl)propyl)-methyl-1-amine, N,N-bis(3-(trimethoxysilyl)propyl)-methyl-1-amine, N,N-bis(3-(triethoxysilyl)propyl)-methyl-1-amine, N,N-diethyl-3-(trimethoxysilyl)propan-1-amine, N,N-diethyl-3-(triethoxysilyl)propan-1-amine, tri(trimethoxysilyl)amine, tri-(3-(trimethoxysilyl)propyl) amine, N,N-bis(3-(diethoxy(methyl)silyl)propyl)-1,1,1-trimethlysilanamine and 3-(dimethoxy(methyl)silyl)-N,N-diethylpropane-1-amine.

In addition, particularly, according to another embodiment of the present invention, the modifier may be a compound represented by Formula 3, and in Formula 3, $A_1$ and $A_2$ may be each independently an alkylene group of 1 to 10 carbon atoms, $R_{25}$ to $R_{28}$ may be each independently an alkyl group of 1 to 10 carbon atoms, and $L_1$ to $L_4$ may be each independently a substituted tetravalent alkylsilyl group with an alkyl group of 1 to 5 carbon atoms, or an alkyl group of 1 to 10 carbon atoms.

In a more particular embodiment, the compound represented by Formula 3 may be one selected from the group consisting of 3,3'-(1,1,3,3-tetramethoxydisiloxane-1,3-diyl)bis(N,N-dimethylpropan-1-amine, 3,3'-(1,1,3,3-tetraethoxydisiloxane-1,3-diyl)bis(N,N-dimethylpropan-1-amine, 3,3'-(1,1,3,3-tetrapropoxydisiloxane-1,3-diyl)bis(N,N-dimethylpropan-1-amine, 3,3'-(1,1,3,3-tetramethoxydisiloxane-1,3-diyl)bis(N,N-diethylpropan-1-amine, 3,3'-(1,1,3,3-tetramethoxydisiloxane-1,3-diyl)bis(N,N-dipropylpropan-1-amine, 3,3'-(1,1,3,3-tetraethoxydisiloxane-1,3-diyl)bis(N,N-diethylpropan-1-amine, 3,3'-(1,1,3,3-tetrapropoxydisiloxane-1,3-diyl)bis(N,N-diethylpropan-1-amine), 3,3'-(1,1,3,3-tetraethoxydisiloxane-1,3-diyl)bis(N,N-dipropylpropan-1-amine, 3,3'-(1,1,3,3-tetrapropoxydisiloxane-1,3-diyl)bis(N,N-dipropylpropan-1-amine, 3,3'-(1,1,3,3-tetramethoxydisiloxane-1,3-diyl)bis(N,N-diethylmethan-1-amine), 3,3'-(1,1,3,3-tetraethoxydisiloxane-1,3-diyl)bis(N,N-diethylmethan-1-amine), 3,3'-(1,1,3,3-tetrapropoxydisiloxane-1,3-diyl)bis(N,N-diethylmethan-1-amine), 3,3'-(1,1,3,3-tetramethoxydisiloxane-1,3-diyl)bis(N,N-dimethylmethan-1-amine), 3,3'-(1,1,3,3-tetramethoxydisiloxane-1,3-diyl)bis(N,N-dipropylmethan-1-amine), 3,3'-(1,1,3,3-tetrapropoxydisiloxane-1,3-diyl)bis(N,N-dimethylmethan-1-amine), 3,3'-(1,1,3,3-tetrapropoxydisiloxane-1,3-diyl)bis(N,N-dipropylmethan-1-amine), 3,3'-(1,1,3,3-tetraethoxydisiloxane-1,3-diyl)bis(N,N-dimethylmethan-1-amine), 3,3'-(1,1,3,3-tetraethoxydisiloxane-1,3-diyl)bis(N,N-dipropylmethan-1-amine), N,N'-((1,1,3,3-tetramethoxydisiloxane-1,3-diyl)bis(propan-3,1-diyl))bis(1,1,1-trimethyl-N-(trimethylsilyl)silanamine), N,N'-((1,1,3,3-tetraethoxydisiloxane-1,3-diyl)bis(propan-3,1-diyl))bis(1,1,1-trimethyl-N-(trimethylsilyl)silanamine), N,N'-((1,1,3,3-tetrapropoxydisiloxane-1,3-diyl)bis(propan-3,1-diyl))bis(1,1,1-trimethyl-N-(trimethylsilyl)silanamine), N,N'-((1,1,3,3-tetramethoxydisiloxane-1,3-diyl)bis(propan-3,1-diyl))bis(1,1,1-trimethyl-N-phenylsilanamine), N,N'-((1,1,3,3-tetraethoxydisiloxane-1,3-diyl)bis(propan-3,1-diyl))bis(1,1,1-trimethyl-N-phenylsilanamine), and N,N'-((1,1,3,3-tetrapropoxydisiloxane-1,3-diyl)bis(propan-3,1-diyl))bis(1,1,1-trimethyl-N-phenylsilanamine).

As described above, the modified conjugated diene-based polymer according to an embodiment of the present invention has a specific structure and may have a specific molecular weight distribution degree and shape. Such a polymer structure may be expressed by physical properties such as a shrinking factor, a mooney stress relaxation ratio, and a coupling number. The molecular weight distribution degree and shape thereof may be expressed by a molecular weight distribution value, the shape of a molecular weight distribution curve, and the coupling number, and the modification of both terminals by a modifier and a modification initiator may influence the structure, and the molecular weight distribution degree and shape thereof. Parameters expressing the structure of such polymer and characteristics relating to the molecular weight distribution may be satisfied by a preparation method which will be described later.

In addition, the above-mentioned characteristics may preferably be satisfied through the preparation method, but only if the above-mentioned all characteristics are satisfied, effects for accomplishing in the present invention may be achieved.

In addition, the present invention provides a method for preparing the modified conjugated diene-based polymer.

The method for preparing the modified conjugated diene-based polymer according to an embodiment of the present invention may include polymerizing a conjugated diene-based monomer, or a conjugated diene-based monomer and an aromatic vinyl monomer in the presence of a modification initiator in a hydrocarbon solvent to prepare an active polymer including a functional group derived from the modification initiator (S1); and reacting or coupling the active polymer prepared in step (S1) with a modifier represented by Formula 2 or Formula 3 below (S2), wherein step (S1) is continuously performed in two or more polymerization reactors, a polymerization conversion ratio in a first reactor among the polymerization reactors is 50% or less, and the modification initiator is a reaction product prepared by reacting a compound represented by Formula 1 below and an organometal compound.

[Formula 1]

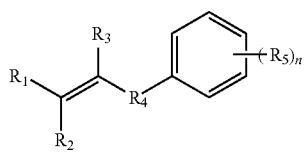

[Formula 2]

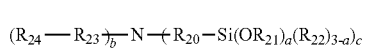

[Formula 3]

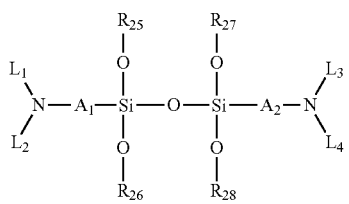

In Formula 1 to Formula 3, $R_1$ to $R_5$, $R_{20}$ to $R_{28}$, $A_1$, $A_2$, $L_1$ to $L_4$, n, a, b and c are the same as defined above.

The hydrocarbon solvent is not specifically limited and may be, for example, one or more selected from the group consisting of n-pentane, n-hexane, n-heptane, isooctane, cyclohexane, toluene, benzene and xylene.

In addition, the conjugated diene-based monomer and the aromatic vinyl monomer are the same as defined above.

According to an embodiment of the present invention, the modification initiator may be used in 0.01 mmol to 10 mmol, 0.05 mmol to 5 mmol, 0.1 mmol to 2 mmol, 0.1 mmol to 1 mmol, or 0.15 mmol to 0.8 mmol based on total 100 g of the monomers.

The polymerization of step (S1) may be, for example, an anionic polymerization, and particularly, a living anionic polymerization by which an anionic active part is formed at the polymerization terminal through a propagation reaction by anions. In addition, the polymerization of step (S1) may be conducted by a polymerization with heating, an isothermal polymerization, or a polymerization at a constant temperature (adiabatic polymerization). The polymerization at a constant temperature means a polymerization method including a step of polymerizing using self-generated heat of reaction without optionally applying heat after adding a polymerization initiator, and the polymerization with heating means a polymerization method including injecting the polymerization initiator and increasing the temperature by optionally applying heat. The isothermal polymerization means a polymerization method by which the temperature of a polymerization reactant is kept constant by applying heat or taking heat after adding the polymerization initiator.

In addition, according to an embodiment of the present invention, the polymerization of step (S1) may be performed by further including a diene-based compound of 1 to carbon atoms in addition to the conjugated diene-based monomer, and in this case, preventing effect of gel formation on the wall side of a reactor after operating for a long time may be achieved. The diene-based compound may be, for example, 1,2-butadiene.

The polymerization of step (S1) may be performed in a temperature range of 80° C. or less, −20° C. to 80° C., 0° C. to 80° C., 0° C. to 70° C., or 10° C. to 70° C., and in this range, the molecular weight distribution of a polymer is controlled narrow, and effect of excellent improvement of physical properties may be achieved.

The active polymer prepared by step (S1) may mean a polymer in which a polymer anion and an organometal cation are coupled.

According to an embodiment of the present invention, the method for preparing a modified conjugated diene-based polymer may be performed in a plurality of reactors including two or more polymerization reactors and a modification reactor by a continuous polymerization method. In a particular embodiment, step (S1) may be performed continuously in two or more polymerization reactors including a first reactor, and the number of the polymerization reactor may be flexibly determined according to reaction conditions and environment. The continuous polymerization method may mean reaction processes of continuously supplying reactants to a reactor and continuously discharging reaction products thus produced. By the continuous polymerization method, effect of excellent productivity and processability, and excellent uniformity of the polymer thus prepared may be achieved.

In addition, according to an embodiment of the present invention, in case where the active polymer is continuously prepared in the polymerization reactor, a polymerization conversion ratio in the first reactor may be 50% or less, from 10% to 50%, or from 20% to 50%, and within this range, side reactions generated while forming a polymer after initiating polymerization reaction may be restrained and a polymer with a linear structure may be induced during polymerization. Thus, the molecular weight distribution of the polymer may be controlled narrow, and effect of excellent improvement of physical properties may be achieved.

In this case, the polymerization conversion ratio may be controlled according to the reaction temperature, the retention time in the reactor, etc.

The polymerization conversion ratio may be determined, for example, by measuring a solid concentration in a polymer solution phase including the polymer during polymerizing a polymer. In a particular embodiment, in order to secure the polymer solution, a cylinder type container is installed at the outlet of each polymerization reactor to fill a certain amount of the polymer solution in the cylinder type container. Then, the cylinder type container is separated from the reactor, the weight (A) of the cylinder filled with the polymer solution is measured, the polymer solution filled in the cylinder type container is transported to an aluminum container, for example, an aluminum dish, the weight (B) of the cylinder type container from which the polymer solution is removed is measured, the aluminum container containing the polymer solution is dried in an oven of 140° C. for 30 minutes, the weight (C) of a dried polymer is measured, and calculation is performed according to the following Mathematical Equation 1:

[Mathematical Equation 1]

$$\text{Polymer conversion ratio } (\%) = \frac{\text{Weight }(C)}{\left[ (\text{Weight }(A) - \text{Weight }(B)) \times \text{total solid content of each reactor (wt \%, } TSC) \right]}$$

Meanwhile, the polymerization reactant polymerized in the first reactor may be transported to a polymerization reactor in front of a modification reactor in order, and polymerization may be performed until the final polymerization conversion ratio becomes 95% or more. After performing the polymerization in the first reactor, the polymerization conversion ratio of the second reactor, or each reactor from the second reactor to the polymerization reactor in front of the modification reactor may be appropriately controlled to control molecular weight distribution.

Meanwhile, in step (S1), during preparing an active polymer, the retention time of a polymerization reactant in the first reactor may be from 1 minute to 40 minutes, from 1 minute to 30 minutes, or from 5 minutes to 30 minutes, and within this range, the control of a polymerization conversion ratio is favorable, and thus, the control of molecular weight distribution of a polymer narrow is possible, and effect of improving physical properties may be excellent.

The term "polymerization reactant" used in the present invention may mean an intermediate of a polymer type, which is under polymerization in each reactor during performing step (S1), after finishing step (S1) or step (S2), prior to obtaining an active polymer or a modified conjugated diene-based polymer, or may mean a polymer of a polymerization conversion ratio of less than 95%, which is under polymerization in a reactor.

According to an embodiment of the present invention, the molecular weight distribution as indicated by a polydispersity index (PDI, Mw/Mn) of the active polymer prepared in step (S1) may be less than 1.5, from 1.0 to less than 1.5, or from 1.1 to less than 1.5, and within this range, the molecular weight distribution of a modified conjugated diene-based polymer which is prepared via a modification reaction or coupling with a modifier is narrow, and improving effect of physical properties may be excellent.

Meanwhile, the polymerization of step (S1) may be performed by including a polar additive, and the polar additive may be added in a ratio of 0.001 g to 50 g, 0.001 g to 10 g, or 0.005 g to 0.1 g based on total 100 g of the monomers. In another embodiment, the polar additive may be added in a ratio of 0.001 g to 10 g, 0.005 g to 5 g, or 0.005 g to 4 g based on total 1 mmol of a modification initiator.

The polar additive may be, for example, one or more selected from the group consisting of tetrahydrofuran, 2,2-di(2-tetrahydrofuryl)propane, diethyl ether, cycloamyl ether, dipropyl ether, ethylene methyl ether, ethylene dimethyl ether, diethyl glycol, dimethyl ether, tert-butoxy ethoxy ethane, bis(3-dimethylaminoethyl)ether, (dimethylaminoethyl) ethyl ether, trimethylamine, triethylamine, tripropylamine, N,N,N',N'-tetramethylethylenediamine, sodium mentholate, and 2-ethyl tetrahydrofurfuryl ether, and may preferably be triethylamine, tetramethyethylenediamine, sodium mentholate, or 2-ethyl tetrahydrofurfuryl ether. If the polar additive is included, and if conjugated diene-based monomer, or a conjugated diene-based monomer and an aromatic vinyl-based monomer are copolymerized, the difference of their reaction rates may be compensated, and effect of inducing easy formation of a random copolymer may be achieved.

According to an embodiment of the present invention, the reaction or coupling of step (S2) may be performed in a modification reactor, and in this case, the modifier may be used in an amount of 0.01 mmol to 10 mmol based on total 100 g of the monomers. In another embodiment, the modifier may be used in a molar ratio of 1:0.1 to 10, 1:0.1 to 5, or 1:0.1 to 1:3 based on 1 mol of the modification initiator of step (Si).

In addition, according to an embodiment of the present invention, the modifier may be injected into a modification reactor, and step (S2) may be performed in the modification reactor. In another embodiment, the modifier may be injected to a transporting part for transporting the active polymer prepared in step (S1) to a modification reactor for performing step (S2), and in the transporting part, reaction or coupling by the mixing of the active polymer and the modifier may be carried out.

Also, the present invention provides a rubber composition including the modified conjugated diene-based polymer.

The rubber composition may include the modified conjugated diene-based polymer in an amount of 10 wt % or more, 10 wt % to 100 wt %, or 20 wt % to 90 wt %, and within this range, mechanical properties such as tensile strength and abrasion resistance are excellent, and effect of excellent balance among each of physical properties may be achieved.

In addition, the rubber composition may include, for example, 0.1 parts by weight to 200 parts by weight, or 10 parts by weight to 120 parts by weight of a filler with respect to 100 parts by weight of the modified conjugated diene-based polymer.

In addition, the rubber composition may include, for example, a process oil, and in this case, the process oil may be included in 20 to 60 parts by weight with respect to 100 parts by weight of the modified conjugated diene-based polymer.

In addition, in another embodiment, the present invention provides a rubber composition including 100 parts by weight of a modified conjugated diene-based polymer and 20 to 60 parts by weight of a process oil, wherein the modified conjugated diene-based polymer has a polymer component with a molecular weight of 100,000 g/mol or more in a standard polystyrene conversion molecular weight by gel permeation chromatography (GPC) having a unimodal shape, a number average molecular weight of 100,000 to 700,000 g/mol, molecular weight distribution of 2.5 or less, an amount of a polymer component having a functional group of 50 wt % or more, the vinyl content of a butadiene unit of 20 mol % to 80 mol %, each of the Si content and the N content of 100 ppm or more based on the weight, a mooney stress relaxation ratio measured at 100° C. of 0.7 or more, and a shrinking factor obtained by measurement by a gel permeation chromatography-light scattering method provided with a viscometer of 1.0 or more.

Meanwhile, in an another embodiment of the present invention, the amount of the polymer component having a functional group shows a modification ratio of a modified conjugated diene-based polymer, for example, the modification ratio may be obtained by measuring each chromatogram using a GPC in which three polystyrene-based gel (Shodex) columns are connected and a GPC in which a silica-based gel column (Zorbax) is connected, and measuring an absorption amount to a silica column from the difference therebetween.

In addition, the rubber composition may further include other rubber component, as necessary, in addition to the modified conjugated diene-based polymer, and in this case, the rubber component may be included in an amount of 90 wt % or less based on the total amount of the rubber composition. In a particular embodiment, the rubber component may be included in an amount of 1 part by weight to 900 parts by weight based on 100 parts by weight of the modified conjugated diene-based copolymer.

The rubber component may be, for example, a natural rubber or a synthetic rubber, and may particularly be a natural rubber (NR) including cis-1,4-polyisoprene; a modified natural rubber which is obtained by modifying or purifying a common natural rubber, such as an epoxidized natural rubber (ENR), a deproteinized natural rubber (DPNR), and a hydrogenated natural rubber; and a synthetic rubber such as a styrene-butadiene copolymer (SBR), a polybutadiene (BR), a polyisoprene (IR), a butyl rubber (IIR), an ethylene-propylene copolymer, a polyisobutylene-co-isoprene, a neoprene, a poly(ethylene-co-propylene), a poly(styrene-co-butadiene), a poly(styrene-co-isoprene), a poly(styrene-co-isoprene-co-butadiene), a poly(isoprene-co-butadiene), a poly(ethylene-co-propylene-co-diene), a polysulfide rubber, an acryl rubber, a urethane rubber, a silicone rubber, an epichlorohydrin rubber, and a halogenated butyl rubber, and any one or a mixture two or more thereof may be used.

The filler may be, for example, a silica-based filler, particularly, wet silica (hydrated silicate), dry silica (anhydrous silicate), calcium silicate, aluminum silicate, or colloid silica. Preferably, the filler may be wet silica which has the most significant improving effect of destruction characteristics and compatible effect of wet grip. In addition, the rubber composition may further include a carbon-based filler, as necessary.

In another embodiment, if silica is used as the filler, a silane coupling agent may be used together for the improvement of reinforcing and low exothermic properties. Particular examples of the silane coupling agent may include bis(3-triethoxysilylpropyl)tetrasulfide, bis(3-triethoxysilyl-propyl)trisulfide, bis(3-triethoxysilylpropyl)disulfide, bis(2- triethoxysilylethyl) tetrasulfide, bis(3-trimethoxysilylpropyl)tetrasulfide, bis(2-trimethoxysilylethyl)tetrasulfide, 3-mercaptopropyltrimethoxysilane, 3-mercaptopropyltriethoxysilane, 2-mercaptoethyltrimethoxysilane, 2-mercaptoethyltriethoxysilane, 3-trimethoxysilylpropyl-N,N-dimethylthiocarbamoyltetrasulfide, 3-triethoxysilylpropyl-N,N-dimethylthiocarbamoyltetrasulfide, 2-triethoxysilylethyl-N,N-dimethylthiocarbamoyltetrasulfide, 3-trimethoxysilylpropylbenzothiazolyltetrasulfide, 3-triethoxysilylpropylbenzolyltetrasulfide, 3-triethoxysilylpropylmethacrylatemonosulfide, 3-trimethoxysilylpropylmethacrylatemonosulfide, bis(3-diethoxymethylsilylpropyl) tetrasulfide, 3-mercaptopropyldimethoxymethylsilane, dimethoxymethylsilylpropyl-N,N-dimethylthiocarbamoyltetrasulfide, or dimethoxymethylsilylpropylbenzothiazolyltetrasulfide, and any one or a mixture of two or more thereof may be used. Preferably, bis(3-triethoxysilylpropyl) polysulfide or 3-trimethoxysilylpropylbenzothiazyltetrasulfide may be used in consideration of the improving effect of reinforcing properties.

In addition, in the rubber composition according to an embodiment of the present invention, since a modified conjugated diene-based polymer in which a functional group having high affinity with silica is brought in an active part is used as a rubber component, the mixing amount of the silane coupling agent may be smaller than a common case. Thus, the silane coupling agent may be used in an amount of 1 part by weight to 20 parts by weight, or 5 parts by weight to 15 parts by weight based on 100 parts by weight of silica. With the amount used in the above range, effect as a coupling agent may be sufficiently exhibited, and preventing effect of gelation of a rubber component may be achieved.

The process oil acts as a softener in a rubber composition, and may include, for example, a paraffin-based, naphthene-based, or aromatic compound. An aromatic process oil may be used in consideration of tensile strength and abrasion resistance, and a naphthene-based or paraffin-based process oil may be used in consideration of hysteresis loss and properties at a low temperature. The process oil may be included in an amount of 100 parts by weight or less based on 100 parts by weight of the rubber component. Within the above-described range, the deterioration of the tensile strength and low exothermic properties (low fuel consumption ratio) of a vulcanized rubber may be prevented.

The rubber composition according to an embodiment of the present invention may be sulfur crosslinkable, and so may further include a vulcanizing agent. The vulcanizing agent may particularly be a sulfur powder and may be included in an amount of 0.1 parts by weight to 10 parts by weight based on 100 parts by weight of a rubber component. With the amount used in the above range, elasticity and strength required for a vulcanized rubber composition may be secured, and at the same time, an excellent low fuel consumption ratio may be achieved.

The rubber composition according to an embodiment of the present invention may further include various additives used in a common rubber industry in addition to the above components, particularly, a vulcanization accelerator, an antioxidant, a plasticizer, an antiaging agent, a scorch preventing agent, a zinc white, stearic acid, a thermosetting resin, or a thermoplastic resin.

The vulcanization accelerator may include, for example, thiazole-based compounds such as 2-mercaptobenzothiazole (M), dibenzothiazyldisulfide (DM), and N-cyclohexyl-2-benzothiazylsulfenamide (CZ), or guanidine-based compounds such as diphenylguanidine (DPG), in an amount of 0.1 parts by weight to 5 parts by weight based on 100 parts by weight of the rubber component.

The antioxidant may include, for example, 2,6-di-t-butyl paracresol, dibutylhydroxytoluene, 2,6-bis((dodecylthio) methyl)-4-nonylphenol or 2-methyl-4,6-bis((octylthio) methyl)phenol, and may be used in an amount of 0.1 parts by weight to 6 parts by weight based on 100 parts by weight of a rubber component.

The antiaging agent may include, for example, N-isopropyl-N'-phenyl-p-phenylenediamine, N-(1,3-dimethylbutyl)-N'-phenyl-p-phenylenediamine, 6-ethoxy-2,2,4-trimethyl-1,2-dihydroquinoline, or a condensate of diphenylamine and acetone at a high temperature, in an amount of 0.1 parts by weight to 6 parts by weight based on 100 parts by weight of the rubber component.

The rubber composition according to an embodiment of the present invention may be obtained by mulling using a mulling apparatus such as a banbury mixer, a roll, and an internal mixer according to a mixing prescription. A rubber composition having low exothermic properties and good abrasion properties may be obtained by a vulcanization process after a molding process.

Therefore, the rubber composition may be useful to the manufacture of each member of a tire such as a tire tread, an under tread, a side wall, a carcass coating rubber, a belt coating rubber, a bead filler, a chafer, and a bead coating rubber, or to the manufacture of rubber products in various industries such as a vibration-proof rubber, a belt conveyor, and a hose.

Also, the present invention provides a tire manufactured using the rubber composition.

The tire may be a tire or a tire including a tire tread.

Hereinafter, the present invention will be explained in more detail referring to embodiments. Embodiments according to the present invention may be modified into various other types, and the scope of the present invention should not be limited to the embodiments described below. The embodiments of the present invention are provided for completely explaining the present invention to a person having an average knowledge in the art.

Preparation Example 1

Two of vacuum dried 4 L stainless steel pressure vessels were prepared. To a first pressure vessel, 985 g of cyclohexane, 120 g of a compound represented by Formula 1-3 below, and 86 g of tetramethylethylenediamine were injected to prepare a first reaction solution. At the same time, to a second pressure vessel, 318 g of a liquid phase 20 wt % n-butyllithium and 874 g of cyclohexane were injected to prepare a second reaction solution. In this case, the molar ratio of the compound represented by Formula 1-3, n-butyllithium and tetramethylethylenediamine was 1:1:1. While keeping the pressure in each pressure vessel to 7 bar, the first reaction solution was injected in an injection rate of 1.0 g/min via a first continuous type channel and the second reaction solution was injected in an injection rate of 1.0 g/min via a second continuous type channel, respectively, into a continuous type reactor using a mass flowmeter. In this case, the temperature of the continuous type reactor was kept to −10° C., the inner pressure was kept to 3 bar using a backpressure regulator, and the retention time in the reactor was controlled to be within 10 minutes. The reaction was finished to obtain a modification initiator.

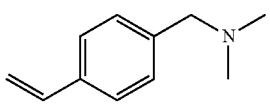

[Formula 1-3]

Preparation Example 2

Two of vacuum dried 4 L stainless steel pressure vessels were prepared. To a first pressure vessel, 944 g of cyclohexane, 161 g of a compound represented by Formula 1-1 below, and 86 g of tetramethylethylenediamine were injected to prepare a first reaction solution. At the same time, to a second pressure vessel, 318 g of a liquid phase 20 wt % n-butyllithium and 874 g of cyclohexane were injected to prepare a second reaction solution. In this case, the molar ratio of the compound represented by Formula 1-1, n-butyllithium and tetramethylethylenediamine was 1:1:1. While keeping the pressure in each pressure vessel to 7 bar, the first reaction solution was injected in an injection rate of 1.0 g/min via a first continuous type channel and the second reaction solution was injected in an injection rate of 1.0 g/min via a second continuous type channel, respectively, into a continuous type reactor using a mass flowmeter. In this case, the temperature of the continuous type reactor was kept to −10° C., the inner pressure was kept to 3 bar using a backpressure regulator, and the retention time in the reactor was controlled to be within 10 minutes. The reaction was finished to obtain a modification initiator.

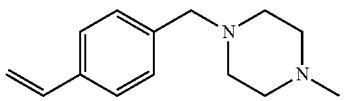

[Formula 1-1]

Preparation Example 3

Two of vacuum dried 4 L stainless steel pressure vessels were prepared. To a first pressure vessel, 898 g of cyclohexane, 207 g of a compound represented by Formula 1-2 below, and 86 g of tetramethylethylenediamine were injected to prepare a first reaction solution. At the same time, to a second pressure vessel, 318 g of a liquid phase 20 wt % n-butyllithium and 874 g of cyclohexane were injected to prepare a second reaction solution. In this case, the molar ratio of the compound represented by Formula 1-2, n-butyllithium and tetramethylethylenediamine was 1:1:1. While keeping the pressure in each pressure vessel to 7 bar, the first reaction solution was injected in an injection rate of 1.0 g/min via a first continuous type channel and the second reaction solution was injected in an injection rate of 1.0 g/min via a second continuous type channel, respectively, into a continuous type reactor using a mass flowmeter. In this case, the temperature of the continuous type reactor was kept to −10° C., the inner pressure was kept to 3 bar using a backpressure regulator, and the retention time in the reactor was controlled to be within 10 minutes. The reaction was finished to obtain a modification initiator.

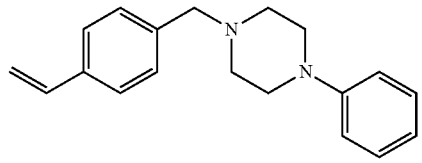

[Formula 1-2]

Example 1

To a first reactor among continuous reactors in which three reactors were connected in series, injected were a styrene solution in which 60 wt % of styrene was dissolved in n-hexane in a rate of 3.08 kg/h, a 1,3-butadiene solution in which 60 wt % of 1,3-butadiene was dissolved in n-hexane in a rate of 12.90 kg/h, n-hexane in a rate of 47.66 kg/h, a 1,2-butadiene solution in which 2.0 wt % of 1,2-butadiene was dissolved in h-hexane in a rate of 10 g/h, a solution in which 10 wt % of 2,2-di(2-tetrahydrofuryl) propane was dissolved in n-hexane as a polar additive in a rate of 10.0 g/h, and the polymerization initiator prepared in Preparation Example 1 in a rate of 292.50 g/h. In this case, the temperature of the first reactor was kept to 50° C., and when a polymerization conversion ratio reached 43%, a polymerization reactant was transported from the first reactor to a second reactor via a transport pipe.

Then, to the second reactor, a 1,3-butadiene solution in which 60 wt % of 1,3-butadiene was dissolved in n-hexane was injected in a rate of 0.68 kg/h. In this case, the temperature of the second reactor was kept to 65° C., and when a polymerization conversion ratio reached 95%, a polymerization reactant was transported from the second reactor to a third reactor via a transport pipe.

The polymerization reactant was transported from the second reactor to the third reactor and a solution in which N,N-bis(3-(diethoxy(methyl)silyl)propyl)-methyl-1-amine was dissolved to was injected as a modifier into the third reactor [modifier:act. Li=1:1 mol]. The temperature of the third reactor was kept to 65° C.

After that, to a polymerization solution discharged from the third reactor, an IR1520 (BASF Co.) solution in which 30 wt % was dissolved was injected as an antioxidant in a rate of 170 g/h and stirred. The polymerization reactant thus obtained was put in hot water heated with steam and stirred to remove solvents to prepare a modified conjugated diene-based polymer.

Example 2

A modified conjugated diene-based polymer was prepared by performing the same procedure in Example 1 except for continuously supplying a solution in which 3,3'-(1,1,3,3-tetramethoxydisiloxane-1,3-diyl)bis(N,N-diethylpropan-1-amine) was dissolved instead of N,N-bis(3-(diethoxy(methyl)silyl)propyl)-methyl-1-amine as a modifier to the third reactor [modifier:act. Li=1:1 mol].

Example 3

A modified conjugated diene-based polymer was prepared by performing the same procedure in Example 1 except for continuously supplying the modification initiator prepared in Preparation Example 2 instead of the modification initiator prepared in Preparation Example 1 as a modification initiator in a rate of 292.5 g/h to the first reactor in Example 1.

Example 4

A modified conjugated diene-based polymer was prepared by performing the same procedure in Example 1 except for continuously supplying the modification initiator prepared in Preparation Example 3 instead of the modification initiator prepared in Preparation Example 1 as a modification initiator in a rate of 292.5 g/h to the first reactor in Example 1.

Example 5

A modified conjugated diene-based polymer was prepared by performing the same procedure in Example 1 except for continuously supplying a solution in which 3-(dimethoxy (methyl)silyl)-N,N-diethylpropane-1-amine was dissolved instead of N,N-bis(3-(diethoxy(methyl)silyl)propyl)-methyl-1-amine as a modifier to the third reactor [modifier:act. Li=1:1 mol].

Example 6

To a first reactor among continuous reactors in which three reactors were connected in series, injected were a styrene solution in which 60 wt % of styrene was dissolved in n-hexane in a rate of 6.58 kg/h, a 1,3-butadiene solution in which 60 wt % of 1,3-butadiene was dissolved in n-hexane in a rate of 9.58 kg/h, n-hexane in a rate of 47.66 kg/h, a 1,2-butadiene solution in which 2.0 wt % of 1,2-butadiene was dissolved in h-hexane in a rate of 10 g/h, a solution in which 10 wt % of 2,2-di(2-tetrahydrofuryl) propane was dissolved in n-hexane as a polar additive in a rate of 10.0 g/h, and the polymerization initiator prepared in Preparation Example 1 in a rate of 292.5 g/h. In this case, the temperature of the first reactor was kept to 50° C., and when a polymerization conversion ratio reached 43%, a polymerization reactant was transported from the first reactor to a second reactor via a transport pipe.

Then, to the second reactor, a 1,3-butadiene solution in which 60 wt % of 1,3-butadiene was dissolved in n-hexane was injected in a rate of 0.50 kg/h. In this case, the temperature of the second reactor was kept to 65° C., and when a polymerization conversion ratio reached 95% or more, a polymerization reactant was transported from the second reactor to a third reactor via a transport pipe.

The polymerization reactant was transported from the second reactor to the third reactor and a solution in which N,N-bis(3-(diethoxy(methyl)silyl)propyl)-methyl-1-amine was dissolved was injected as a modifier to the third reactor [modifier:act. Li=1:1 mol]. The temperature of the third reactor was kept to 65° C.

After that, to a polymerization solution discharged from the third reactor, an IR1520 (BASF Co.) solution in which 30 wt % was dissolved was injected as an antioxidant in a rate of 167 g/h and stirred. The polymerization reactant thus obtained was put in hot water heated with steam and stirred to remove solvents to prepare a modified conjugated diene-based polymer.

Example 7

A modified conjugated diene-based polymer was prepared by performing the same procedure in Example 6 except for transporting a polymerization reactant from the first reactor to the second reactor via a transport pipe when a polymerization conversion ratio reached 41%, and continuously supplying a solution in which 3,3'-(1,1,3,3-tetramethoxy-disiloxane-1,3-diyl)bis(N,N-diethylpropan-1-amine was dissolved as a modifier to the third reactor [modifier:act. Li=1:1 mol].

Comparative Example 1

To a 20 L autoclave reactor, 100 g of styrene, 346 g of 1,3-butadiene, 2500 g of n-hexane and 0.78 g of 2,2-di(2-tetrahydrofuryl)propane as a polar additive were injected, and the internal temperature of the reactor was elevated to 50° C. After the internal temperature of the reactor reached 50° C., 226.7 g of the polymerization initiator prepared in Preparation Example 1 was injected and an adiabatic reaction with heating was performed. After about 20 minutes lapse, 18.2 g of 1,3-butadiene was injected for capping the terminals of a polymer chain with butadiene. After 5 minutes, a solution in which 3-(dimethoxy(methyl)silyl)-N,N-diethylpropan-1-amine was dissolved was injected as a modifier to the reactor and reacted for 15 minutes [modifier: act. Li=1:1 mol]. Then, the polymerization reaction was quenched by using ethanol, and 2.35 g of an IR1520 (BASF Co.) antioxidant was added thereto. The polymerization reactant thus obtained was injected into hot water heated using steam and stirred to remove solvents to prepare a modified styrene-butadiene copolymer.

Comparative Example 2

To a first reactor among continuous reactors in which three reactors were connected in series, injected were a styrene solution in which 60 wt % of styrene was dissolved in n-hexane in a rate of 3.08 kg/h, a 1,3-butadiene solution in which 60 wt % of 1,3-butadiene was dissolved in n-hexane in a rate of 12.90 kg/h, n-hexane in a rate of 47.66 kg/h, a 1,2-butadiene solution in which 2.0 wt % of 1,2-butadiene was dissolved in h-hexane in a rate of 10 g/h, a solution in which 10 wt % of 2,2-di(2-tetrahydrofuryl) propane was dissolved in n-hexane as a polar additive in a rate of 10.0 g/h, and a n-butyllithium solution in which 15 wt % of n-butyllithium was dissolved in n-hexane as a polymerization initiator in a rate of 39.0 g/h. In this case, the temperature of the first reactor was kept to 55° C., and when a polymerization conversion ratio reached 48%, a polymerization reactant was transported from the first reactor to a second reactor via a transport pipe.

Then, to the second reactor, a 1,3-butadiene solution in which 60 wt % of 1,3-butadiene was dissolved in n-hexane was injected in a rate of 0.68 kg/h. In this case, the temperature of the second reactor was kept to 65° C., and when a polymerization conversion ratio reached 95% or more, a polymerization reactant was transported from the second reactor to a third reactor via a transport pipe.

The polymerization reactant was transported from the second reactor to the third reactor and a solution in which dichlorodimethylsilane was dissolved was injected as a coupling agent to the third reactor [coupling agent:act. Li=1:1 mol]. The temperature of the third reactor was kept to 65° C.

After that, to a polymerization solution discharged from the third reactor, an IR1520 (BASF Co.) solution in which 30 wt % was dissolved was injected as an antioxidant in a rate of 170 g/h and stirred. The polymerization reactant thus obtained was put in hot water heated with steam and stirred to remove solvents to prepare a modified conjugated diene-based polymer.

Comparative Example 3

To a first reactor among continuous reactors in which three reactors were connected in series, injected were a styrene solution in which 60 wt % of styrene was dissolved in n-hexane in a rate of 6.58 kg/h, a 1,3-butadiene solution in which 60 wt % of 1,3-butadiene was dissolved in n-hexane in a rate of 9.58 kg/h, n-hexane in a rate of 47.66 kg/h, a 1,2-butadiene solution in which 2.0 wt % of 1,2-butadiene was dissolved in h-hexane in a rate of 10 g/h, a solution in which 10 wt % of 2,2-di(2-tetrahydrofuryl) propane was dissolved in n-hexane as a polar additive in a rate of 10.0 g/h, and a n-butyllithium solution in which 15 wt % of n-butyllithium was dissolved in n-hexane as a polymerization initiator in a rate of 39.0 g/h. In this case, the temperature of the first reactor was kept to 55° C., and when a polymerization conversion ratio reached 48%, a polymerization reactant was transported from the first reactor to a second reactor via a transport pipe.

Then, to the second reactor, a 1,3-butadiene solution in which 60 wt % of 1,3-butadiene was dissolved in n-hexane was injected in a rate of 0.50 kg/h. In this case, the temperature of the second reactor was kept to 65° C., and when a polymerization conversion ratio reached 95% or more, a polymerization reactant was transported from the second reactor to a third reactor via a transport pipe.

The polymerization reactant was transported from the second reactor to the third reactor and a solution in which dichlorodimethylsilane was dissolved as a coupling agent was injected to the third reactor [coupling agent:act. Li=1:1 mol]. The temperature of the third reactor was kept to 65° C.

After that, to a polymerization solution discharged from the third reactor, an IR1520 (BASF Co.) solution in which 30 wt % was dissolved was injected as an antioxidant in a rate of 167 g/h and stirred. The polymerization reactant thus obtained was put in hot water heated with steam and stirred to remove solvents to prepare a modified conjugated diene-based polymer.

Comparative Example 4

A modified conjugated diene-based polymer was prepared by performing the same procedure in Example 1 except for keeping the temperature of the first reactor to 75° C. and transporting the polymerization reactant from the first reactor to the second reactor via the transport pipe when the polymerization conversion ratio reached 70% in Example 1.

Comparative Example 5

A conjugated diene-based polymer was prepared by performing the same procedure in Example 1 except for not injecting the solution in which N,N-bis(3-(diethoxy(methyl) silyl)propyl)-methyl-1-amine was dissolved to the third reactor in Example 1.

Comparative Example 6

A modified conjugated diene-based polymer was prepared by performing the same procedure in Example 1 except for continuously injecting a n-butyllithium solution in which 15 wt % of n-butyllithium was dissolved in n-hexane instead of the polymerization initiator prepared in Preparation Example 1 in a rate of 39.0 g/h to the first reactor in Example 1.

Reference Example 1

A modified conjugated diene-based polymer was prepared by performing the same procedure in Comparative Example 1 except for injecting 8 mol of 3-(dimethoxy(methyl)silyl)-N,N-diethylpropan-1-amine with respect to 1 mol of the active lithium of the modification initiator in Comparative Example 1 (modifier:act. Li=8:1 mol).

Reference Example 2

A modified conjugated diene-based polymer was prepared by performing the same procedure in Comparative Example 1 except for injecting 0.2 mol of 3-(dimethoxy(methyl) silyl)-N,N-diethylpropan-1-amine with respect to 1 mol of the active lithium of the modification initiator in Comparative Example 1 (modifier:act. Li=0.2:1 mol).

Experimental Example 1

With respect to each of the modified or unmodified conjugated diene-based polymers prepared in the Examples, Comparative Examples, and Reference Examples, styrene unit and vinyl content in each polymer, a weight average molecular weight (Mw, $\times 10^3$ g/mol), a number average molecular weight (Mn, $\times 10^3$ g/mol), molecular weight distribution (PDI, MWD), coupling number (C.N.), mooney viscosity (MV), a mooney stress relaxation ratio, a shrinking factor, the Si content and the N content were measured. The results are shown in Table 1 and Table 2 below.

1) Styrene Unit and Vinyl Content (wt %)

The styrene unit (SM) and vinyl content in each polymer were measured and analyzed using Varian VNMRS 500 MHz NMR.

When measuring NMR, 1,1,2,2-tetrachloroethanol was used as a solvent, and the styrene unit and vinyl content were calculated by calculating a solvent peak as 5.97 ppm, and regarding 7.2-6.9 ppm as a random styrene peak, 6.9-6.2 ppm as a block styrene peak, 5.8-5.1 ppm as a 1,4-vinyl peak, and 5.1-4.5 ppm as a 1,2-vinyl peak.

2) Weight average molecular weight (Mw, $\times 10^3$ g/mol), number average molecular weight (Mn, $\times 10^3$ g/mol), polydispersity index (PDI) and coupling number (C.N.)

By gel permeation chromatography (GPC) analysis, the weight average molecular weight (Mw) and the number average molecular weight (Mn) were measured and a molecular weight distribution curve was obtained. In addition, the molecular polydispersity index (PDI, Mw/Mn) was calculated from each of the weight average molecular weight and the number average molecular weight thus measured. Particularly, GPC was conducted using two columns of PLgel Olexis (Polymer Laboratories Co.) and one column of PLgel mixed-C (Polymer Laboratories Co.) in combination, and polystyrene (PS) as a GPC standard material for calculating the molecular weight. A solvent for measuring GPC was prepared by mixing tetrahydrofuran with 2 wt % of an amine compound. In this case, the molecular weight distribution curves thus obtained are shown in FIG. 1 to FIG. 5.

In addition, the coupling number was calculated by collecting a portion of a polymerization reactant prior to injecting a modifier or a coupling agent in each of the Examples and the Comparative Examples and obtaining a peak molecular weight (MP$_1$) of the polymer, then, obtaining the peak molecular weight (Mp$_2$) of each modified conjugated diene-based polymer, and calculating according to the following Mathematical Formula 3:

Coupling number(C.N.)=Mp$_2$/Mp$_1$     [Mathematical Formula 3]

3) Mooney Viscosity and Mooney Stress Relaxation Ratio

The mooney viscosity (MV, (ML1+4, @100° C.) MU) was measured by using MV-2000 (Alpha Technologies Co.) using Large Rotor at a rotor speed of 2±0.02 rpm at 100° C. In this case, a specimen used was stood at room temperature (23±3° C.) for 30 minutes or more, and 27±3 g of the specimen was collected and put in a die cavity, and then, Platen was operated for measurement.

After measuring the mooney viscosity, a gradient value (absolute value) of the mooney viscosity change shown while releasing torque was measured, and the mooney stress relaxation ratio was obtained from the absolute value thereof.

4) Si Content

The Si content was measured by an ICP analysis method, which used an inductively coupled plasma optical emission spectroscopy (ICP-OES; Optima 7300DV). Particularly, measurement was performed by adding about 0.7 g of a specimen to a platinum (Pt) crucible and adding about 1 ml of concentrated sulfuric acid (98 wt %, electronic grade) thereto, heating at 300° C. for 3 hours, incinerating the specimen in an electrical furnace (Thermo Scientific, Lindberg Blue M) by the following program of steps 1 to 3:

1) step 1: initial temp 0° C., rate (temp/hr) 180° C./hr, temp (holdtime) 180° C. (1 hr)

2) step 2: initial temp 180° C., rate (temp/hr) 85° C./hr, temp (holdtime) 370° C. (2 hr)

3) step 3: initial temp 370° C., rate (temp/hr) 47° C./hr, temp (holdtime) 510° C. (3 hr), adding 1 ml of concentrated nitric acid (48 wt %) and 20 µl of concentrated hydrofluoric acid (50 wt %) to a residue, sealing the platinum crucible and shaking for 30 minutes or more, adding 1 ml of boric acid to the specimen, storing at 0° C. for 2 hours or more, diluting in 30 ml of ultrapure water, and performing incineration.

5) N Content

The N content was measured via an NSX analysis method, using a quantitative analyzer of a trace amount of nitrogen (NSX-2100H). Particularly, the quantitative analyzer of a trace amount of nitrogen (Auto sampler, Horizontal furnace, PMT & Nitrogen detector) was turned on, carrier gas flowing amounts were set such that Ar was 250 ml/min, O$_2$ was 350 ml/min, and ozonizer was 300 ml/min, heater was set to 800° C., and the analyzer was stood for about 3 hours for stabilization. After the analyzer was stabilized, a calibration curve in calibration ranges of 5 ppm, 10 ppm, 50 ppm, 100 ppm and 500 ppm was made using nitrogen standard (AccuStandard S-22750-01-5 ml), an area corresponding to each concentration was obtained, and a straight line was obtained using a ratio of concentration vs. area. Then, a ceramic boat holding 20 mg of a specimen was put on the auto sampler of the analyzer and measurement was performed to obtain an area. The N content was calculated using the area of the specimen thus obtained and the calibration curve.

6) Shrinking Factor (g')

The shrinking factor was obtained as follows. A specimen was injected to a GPC-light scattering measurement apparatus (Viscotek TDAmax, Malvern Co.) provided with a light scattering detector in which two columns filled with a polystyrene-based gel as a filler were connected and a viscometer, and an absolute molecular weight was obtained from the light scattering detector, intrinsic viscosity [η] with respect to the absolute molecular weight was obtained from the light scattering detector and the viscometer, intrinsic viscosity [η]$_0$ of a linear polymer with respect to the absolute molecular weight was computed through Mathematical Formula 2 below, and an average value of the ratio of intrinsic viscosity ([η]/[η]$_0$) corresponding to each absolute molecular weight was represented as the shrinking factor. In this case, measurement was performed using a mixture solution of tetrahydrofuran and N,N,N',N'-tetramethylethylenediamine (adjusted by mixing 20 ml of N,N,N',N'-tetramethylethylenediamine with 1 L of tetrahydrofuran) as an eluent, and PL Olexix (Agilent Co.) as a column under conditions of an oven temperature of 40° C. and a THF flow rate of 1.0 ml/min. A specimen was prepared by dissolving 15 mg of a polymer in 10 ml of THF.

$[\eta]_0 = 10^{-3.883} M^{0.771}$     [Mathematical Formula 2]

In Mathematical Formula 2, M is an absolute molecular weight.

TABLE 1

| | Division | Example 1 | Example 2 | Example 3 | Example 4 | Example 5 | Reference Example 1 |
|---|---|---|---|---|---|---|---|
| Reaction conditions | Initiator | a | a | b | c | a | a |
| | Modifier or coupling agent | A | B | A | A | C | C |
| | First reactor temp (° C.) | 50 | 50 | 50 | 50 | 50 | 50→80 |
| | First reactor polymerization conversion ratio (%) | 43 | 43 | 43 | 43 | 43 | batch |
| NMR (wt %) | SM | 18 | 18 | 18 | 18 | 18 | 18 |
| | Vinyl | 47 | 47 | 47 | 47 | 47 | 47 |
| GPC | Mw (×10$^3$ g/mol) | 464 | 471 | 454 | 464 | 442 | 314 |
| | Mn (×10$^3$ g/mol) | 305 | 308 | 295 | 298 | 289 | 273 |
| | PDI | 1.52 | 1.53 | 1.54 | 1.56 | 1.53 | 1.15 |
| | C.N. | 1.7 | 1.8 | 1.8 | 1.7 | 1.7 | 1.0 |

TABLE 1-continued

| | | | | | | |
|---|---|---|---|---|---|---|
| Molecular weight distribution curve | Unimodal | Unimodal | Unimodal | Unimodal | Unimodal | Unimodal |
| Mooney viscosity (MV) | 56 | 56 | 54 | 53 | 55 | 45 |
| Mooney stress relaxation ratio | 1.133 | 1.126 | 1.180 | 1.142 | 1.171 | 1.068 |
| Shrinking factor (g') | 1.082 | 1.070 | 1.132 | 1.067 | 1.064 | 1.069 |
| Si content (ppm) | 225 | 225 | 215 | 210 | 110 | 110 |
| N content (ppm) | 112 | 170 | 169 | 160 | 111 | 110 |

| | | Reference Example | Comparative Example | | | | |
|---|---|---|---|---|---|---|---|
| | Division | 2 | 1 | 2 | 4 | 5 | 6 |
| Reaction conditions | Initiator | a | a | d | a | a | d |
| | Modifier or coupling agent | C | C | D | A | — | A |
| | First reactor temp (° C.) | 50→80 | 50→80 | 55 | 75 | 50 | 50 |
| | First reactor polymerization conversion ratio (%) | batch | batch | 47 | 70 | 45 | 43 |
| NMR (wt %) | SM | 18 | 18 | 18 | 18 | 18 | 18 |
| | Vinyl | 47 | 47 | 47 | 47 | 47 | 47 |
| GPC | Mw (×10³ g/mol) | 498 | 494 | 471 | 575 | 444 | 453 |
| | Mn (×10³ g/mol) | 380 | 341 | 310 | 311 | 300 | 287 |
| | PDI | 1.31 | 1.45 | 1.52 | 1.85 | 1.48 | 1.58 |
| | C.N. | 2.0 | 1.8 | 1.55 | 1.5 | — | 1.6 |
| Molecular weight distribution curve | | Unimodal | bimodal | Unimodal | Unimodal | Unimodal | Unimodal |
| Mooney viscosity (MV) | | 62 | 59 | 57 | 64 | 52 | 60 |
| Mooney stress relaxation ratio | | 1.058 | 1.065 | 1.038 | 0.635 | 1.487 | 1.129 |
| Shrinking factor (g') | | 1.053 | 1.063 | 1.075 | 0.599 | 1.456 | 1.075 |
| Si content (ppm) | | 50 | 115 | 25 | 123 | — | 215 |
| N content (ppm) | | 52 | 110 | — | 85 | 60 | 62 |

TABLE 2

| | | Example | | Comparative Example |
|---|---|---|---|---|
| | Division | 6 | 7 | 3 |
| Reaction conditions | Initiator | a | a | d |
| | Modifier or coupling agent | A | B | D |
| | First reactor temp (° C.) | 50 | 50 | 55 |
| | First reactor polymerization conversion ratio (%) | 43 | 41 | 46 |
| NMR (wt %) | SM | 39 | 39 | 39 |
| | Vinyl | 25 | 25 | 25 |
| GPC | Mw (×10³ g/mol) | 506 | 492 | 479 |
| | Mn (×10³ g/mol) | 320 | 306 | 313 |
| | PDI | 1.58 | 1.61 | 1.53 |
| | C.N. | 1.7 | 1.7 | 1.5 |
| Molecular weight distribution curve | | Unimodal | Unimodal | Unimodal |
| Mooney viscosity (MV) | | 55 | 54 | 58 |
| Mooney stress relaxation ratio | | 1.232 | 1.192 | 0.982 |
| Shrinking factor (g') | | 1.200 | 1.133 | 0.947 |
| Si content (ppm) | | 220 | 223 | 30 |
| N content (ppm) | | 112 | 170 | — |

In Table 1 and Table 2 above, particular materials used as the initiator, modifier and coupling agent are as follows.

Initiator a: modification initiator prepared in Preparation Example 1

Initiator b: modification initiator prepared in Preparation Example 2

Initiator c: modification initiator prepared in Preparation Example 3

Initiator d: n-butyllithium

Modifier A: N,N-bis(3-(diethoxy(methyl)silyl)propyl)-methyl-1-amine

Modifier B: 3,3'-(1,1,3,3-tetramethoxydisiloxane-1,3-diyl)bis(N,N-diethylpropane-1-amine)

Modifier C: 3-(dimethoxy(methyl)silyl)-N,N-diethylpropan-1-amine

Coupling agent D: dichlorodimethylsilane

As shown in Table 1 and Table 2 above, it was found that the modified conjugated diene-based polymers of Examples 1 to 7 according to the embodiments of the present invention have a unimodal shape molecular weight distribution curve by gel permeation chromatography (see FIG. 1 and FIG. 2), a PDI (molecular weight distribution) of 1.0 to less than 1.7, a Si content and N content of 50 ppm or more, a mooney stress relaxation ratio of 0.7 or more, and a shrinking factor of 1.0 or more. In contrast, it was found that the unmodified or modified conjugated diene-based polymers of Comparative Example 1 to Comparative Example 5 have a bimodal shape molecular weight distribution curve by gel permeation chromatography (see FIG. 3), a mooney stress relaxation ratio of less than 0.7, a shrinking factor of less than 1.0, a Si content of less than 50 ppm and a N content of less than 50 ppm. Particularly, Comparative Example 4 in which continuous polymerization was performed but polymerization conversion ratio in the first reactor deviated from the range of the present invention, was found to have a PDI value of greater than 1.7, and the mooney stress relaxation ratio and the shrinking factor of less than 0.7, respectively, which were markedly decreased values when compared with the Examples.

Figure 3:
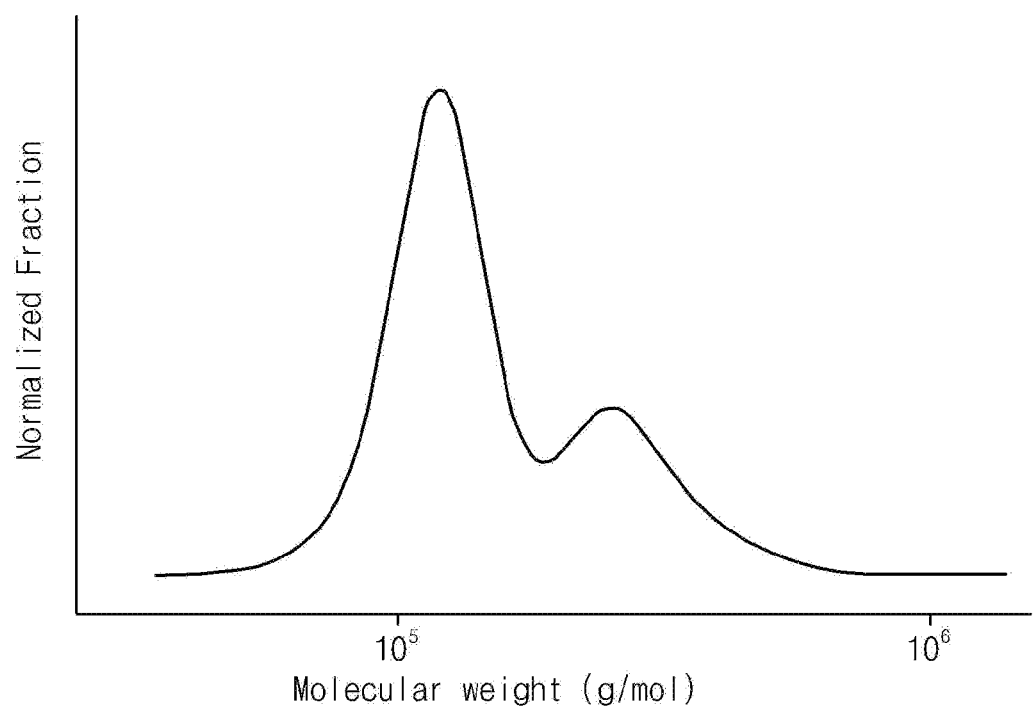
FIG. 3 shows a molecular weight distribution curve by gel permeation chromatography (GPC) of a modified conjugated diene-based polymer of Comparative Example 1 according to an embodiment of the present invention.
Figure 4:
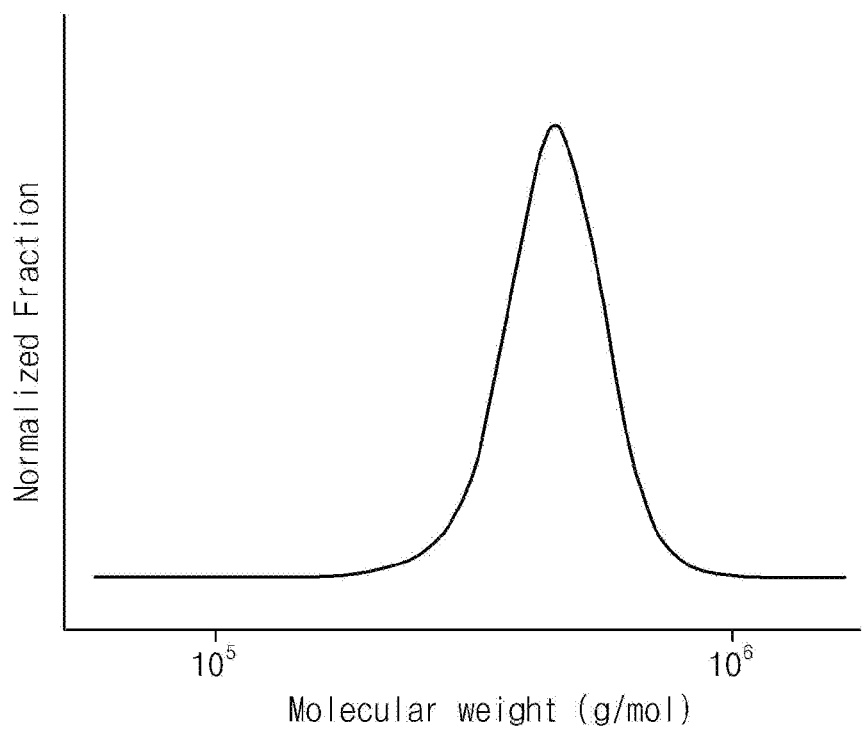
FIG. 4 shows a molecular weight distribution curve by gel permeation chromatography (GPC) of a modified conjugated diene-based polymer of Reference Example 1 according to an embodiment of the present invention.
Figure 5:
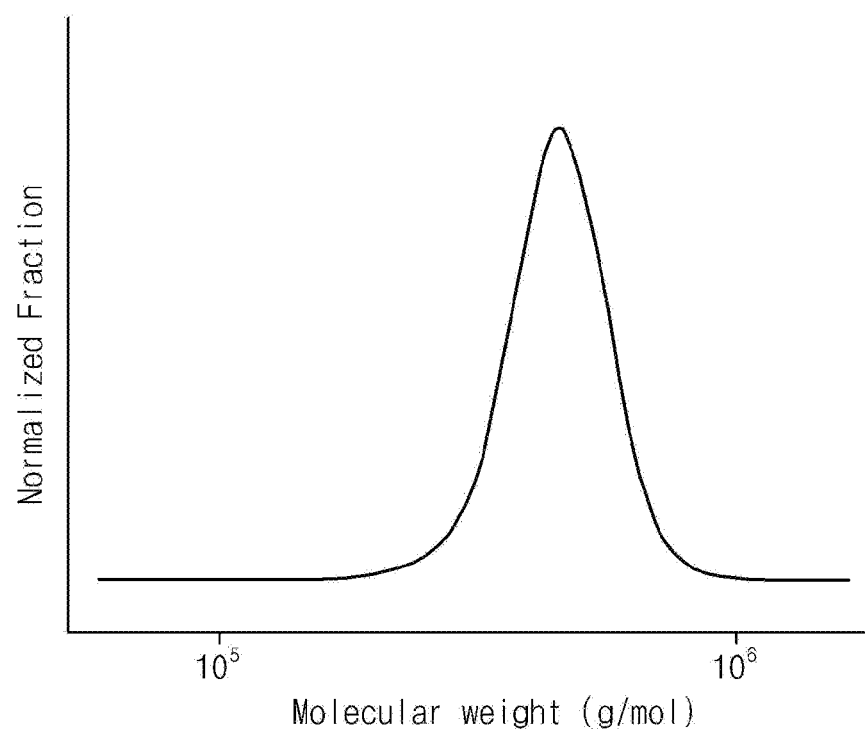
FIG. 5 shows a molecular weight distribution curve by gel permeation chromatography (GPC) of a modified conjugated diene-based polymer of Reference Example 2 according to an embodiment of the present invention.

In addition, Comparative Example 1 in which the same modification initiator and modifier as in Example 5 of the present invention were applied but a polymer was prepared by a batch polymerization method, showed a bimodal shape molecular weight distribution curve by gel permeation chromatography (see FIG. 3). Meanwhile, the molecular weight distribution curve might be controlled to show a unimodal shape though a batch polymerization method was applied as in Reference Examples 1 and 2 (see FIG. 4 and FIG. 5), but in this case, the coupling numbers of the polymers were 1.0 and 2.0, respectively, and only a case where all polymers were not coupled by a modifier (Reference Example 1) and a case where all polymers were coupled by a modifier (Reference Example 2) were present, and thus, the polymers have different structure and properties from the unimodal polymer according to the continuous polymerization method of the present invention. As confirmed in Table 4, which will be described later, it may be found that processability, tensile properties and viscoelasticity properties were inferior to those of Example 5.

Meanwhile, the polymer of Comparative Example 5 was prepared under the same conditions as in Example 1 except for not using the modifier suggested in an embodiment of the present invention, and the modified conjugated diene-based polymer of Comparative Example 6 was prepared under the same conditions as in Example 1 except for the initiator used for polymerization, i.e., prepared by not applying the modifier and the modification initiator suggested in the present invention, and the polymer thus prepared did not include functional groups derived from the modifier and the modification initiator at the same time. Accordingly, as confirmed in Table 4 below, compounding properties with a filler was inferior, and tensile properties and viscoelasticity properties were markedly degraded when compared with those of the Examples.

Experimental Example 2

In order to comparatively analyze the physical properties of rubber compositions including each of modified or unmodified copolymers prepared in the Examples, Comparative Examples and Reference Examples, and molded articles manufactured therefrom, tensile properties and viscoelasticity properties were measured, and the results are shown in Table 4 and Table 5 below.

1) Preparation of Rubber Specimen

Blending was performed using each of the modified or unmodified conjugated diene-based polymers of the Examples, Comparative Examples and Reference Examples as raw material rubber under the blending conditions listed in Table 3 below. The raw materials in Table 3 are represented by parts by weight based on 100 parts by weight of the raw material rubber.

TABLE 3

| Division | Raw material | Amount (parts by weight) |
| --- | --- | --- |
| First stage mulling | Rubber | 100 |
| | Silica | 70 |
| | Coupling agent (X50S) | 11.2 |
| | Process oil | 37.5 |
| | Zinc white | 3 |
| | Stearic acid | 2 |
| | Antioxidant | 2 |

TABLE 3-continued

| Division | Raw material | Amount (parts by weight) |
| --- | --- | --- |
| | Antiaging agent | 2 |
| | wax | 1 |
| Second stage mulling | Sulfur | 1.5 |
| | Rubber accelerator | 1.75 |
| | Vulcanization accelerator | 2 |

Particularly, the rubber specimen was mulled via a first stage mulling and a second stage mulling. In the first stage mulling, a raw material rubber, silica (filler), an organic silane coupling agent, a process oil, zinc oxide, stearic acid, an antioxidant, an antiaging agent and wax were mulled using a banbury mixer equipped with a temperature controlling apparatus. In this case, the initial temperature of a mulling apparatus was controlled to 70° C., and after finishing mixing, a first compound mixture was obtained at a discharge temperature of 145° C. to 155° C. In the second stage mulling, the first compound mixture was cooled to room temperature, and the first compound mixture, sulfur, a rubber accelerator, and a vulcanization accelerator were added to the mulling apparatus and mixed at a temperature of 100° C. or less to obtain a second compound mixture. Then, via a curing process at 160° C. for 20 minutes, a rubber specimen was formed.

2) Tensile Properties

The tensile properties were measured by manufacturing each specimen and measuring tensile strength when broken and tensile stress when elongated by 300% (300% modulus) of each specimen according to an ASTM 412 tensile test method. Particularly, tensile properties were measured using a Universal Test Machin 4204 tensile tester (Instron Co.) in a rate of 50 cm/min at room temperature.

3) Viscoelasticity Properties

The viscoelasticity properties were secured by measuring viscoelasticity behavior on thermodynamic deformation at each measurement temperature (−60° C.-60° C.) with a frequency of 10 Hz by using a dynamic mechanical analyzer (GABO Co.) in a film tension mode and securing a tan δ value. Each of the resultant values of Example 1 to Example 5 were indexed by setting the resultant value of Comparative Example 2 to 100. Each of the resultant values of Examples 6 and 7 were indexed by setting the resultant value of Comparative Example 3 to 100. In this case, if the tan δ vale at a low temperature of 0° C. increases, wet skid resistance becomes better, and if the tan δ value at a high temperature of 60° C. increases, hysteresis loss decreases, and low running resistance (fuel consumption ratio) becomes better.

4) Processability Properties

By measuring the mooney viscosity (MV, (ML 1+4, @100° C.) MU) of the secondary mixture compound obtained during preparing the 1) rubber specimen, the processability properties of each polymer were comparatively analyzed, and in this case, the lower the measured value of the moony viscosity was, the better the processability properties were.

Particularly, by using MV-2000 (Alpha Technologies Co.) using Large Rotor at a rotor speed of 2±0.02 rpm at 100° C., each secondary mixture compound was stood at room temperature (23±3° C.) for 30 minutes or more, and 27±3 g was collected and put in a die cavity, and then, Platen was operated for 4 minutes for measurement.

TABLE 4

| | Division | Example | | | | | Reference Example | | Comparative Example | | | | |
|---|---|---|---|---|---|---|---|---|---|---|---|---|---|
| | | 1 | 2 | 3 | 4 | 5 | 1 | 2 | 1 | 2 | 4 | 5 | 6 |
| Tensile properties | Tensile strength (kgf/cm$^2$) | 188 | 189 | 191 | 188 | 187 | 180 | 180 | 178 | 185 | 183 | 185 | 186 |
| | 300% modulus (kgf/cm$^2$) | 98 | 98 | 97 | 97 | 98 | 72 | 75 | 80 | 70 | 80 | 77 | 84 |
| Viscoelasticity properties | tan δ (at 0° C.) | 103 | 101 | 102 | 101 | 102 | 99 | 101 | 100 | 100 | 100 | 102 | 99 |
| | tan δ (at 60° C.) | 134 | 133 | 135 | 132 | 132 | 110 | 105 | 129 | 100 | 123 | 115 | 119 |
| | Processability properties | 81 | 80 | 80 | 81 | 82 | 97 | 92 | 92 | 72 | 89 | 80 | 81 |

In Table 4, the resultant values of viscoelasticity properties of Example 1 to Example 5, Comparative Example 1, Comparative Examples 4 to 6, and Reference Examples 1 and 2 were indexed (%) and shown on the basis of the measured values of viscoelasticity properties of Comparative Example 2.

TABLE 5

| | Division | Example | | Comparative Example |
|---|---|---|---|---|
| | | 6 | 7 | 3 |
| Tensile properties | Tensile strength (kgf/cm$^2$) | 185 | 186 | 185 |
| | 300% modulus (kgf/cm$^2$) | 114 | 116 | 85 |
| Viscoelasticity properties | tan δ (at 0° C.) | 101 | 102 | 100 |
| | tan δ (at 60° C.) | 132 | 134 | 100 |
| | Processability properties | 82 | 83 | 75 |

In Table 5, the resultant values of Examples 6 and 7 were indexed (%) and shown on the basis of the measured values of viscoelasticity properties of Comparative Example 3.

As shown in Table 4 and Table 5, tensile properties, viscoelasticity properties and processability properties of Example 1 to Example 7 according to the embodiments of the present invention were all excellent in balance when compared with Comparative Example 1 to Comparative Example 6.

Meanwhile, with respect to the viscoelasticity properties, generally, it is known that the increase of a tan δ value at 0° C. together with a tan δ value at 60° C. is very difficult. Accordingly, when compared with Comparative Example 1 to Comparative Example 6, Example 1 to Example 7 showing equal or better degree of a tan δ value at 0° C. and remarkably improved effect of a tan δ value at 60° C., are confirmed to have very excellent viscoelasticity properties.

In addition, as shown in Table 4, in case where a polymer was prepared by batch polymerization but showed a unimodal shape molecular weight distribution curve as in Reference Examples 1 and 2, it was found that the intrinsic inferior processability properties of the batch polymerization were not improved and excellent compounding properties which might be achieved by the batch polymerization were not achieved. Here, the intrinsic inferior processability properties of the batch polymerization could be confirmed from the results of Comparative Example 1 in which common batch polymerization was performed and a bimodal shape molecular weight distribution curve was obtained. Particularly, in Reference Example 1, the mooney viscosity of a mixture compounded was increased by 18% degree when compared with Example 5, and markedly decreased processability properties were shown and markedly decreased 300% modulus and tan δ value at 60° C. were shown to about 30% degrees, respectively. In addition, in Reference Example 2, the mooney viscosity of a mixture compounded was increased by 14% degree and processability properties were markedly decreased when compared with Example 5. At the same time, tensile properties (300% modulus) and viscoelasticity properties (tan δ value at 60°) were markedly decreased as in Reference Example 1.

The invention claimed is:
1. A modified conjugated diene-based polymer, comprising:
a functional group derived from a modification initiator at one terminal; and
a functional group derived from a modifier represented by the following Formula 2 or Formula 3 at the other terminal,
wherein the modification initiator is a reaction product of a compound represented by the following Formula 1 and an organometal compound:

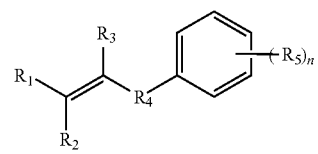

[Formula 1]

in Formula 1,
R$_1$ to R$_3$ are each independently hydrogen; an alkyl group of 1 to 30 carbon atoms; an alkenyl group of 2 to 30 carbon atoms; an alkynyl group of 2 to 30 carbon atoms; a heteroalkyl group of 1 to 30 carbon atoms, a heteroalkenyl group of 2 to 30 carbon atoms; a heteroalkynyl group of 2 to 30 carbon atoms; a cycloalkyl group of 5 to 30 carbon atoms; an aryl group of 6 to 30 carbon atoms; or a heterocyclic group of 3 to 30 carbon atoms,
R$_4$ is a single bond; a substituted or unsubstituted alkylene group of 1 to 20 carbon atoms with a substituent; a substituted or unsubstituted cycloalkylene group of 5 to 20 carbon atoms with a substituent; or a substituted or unsubstituted arylene group of 5 to 20 carbon atoms with a substituent, wherein the substituent is an alkyl group of 1 to 10 carbon atoms, a cycloalkyl group of 5 to 10 carbon atoms, or an aryl group of 6 to 20 carbon atoms,
R$_5$ is an alkyl group of 1 to 30 carbon atoms; an alkenyl group of 2 to 30 carbon atoms; an alkynyl group of 2 to 30 carbon atoms; a heteroalkyl group of 1 to 30 carbon atoms; a heteroalkenyl group of 2 to 30 carbon atoms; a heteroalkynyl group of 2 to 30 carbon atoms;

a cycloalkyl group of 5 to 30 carbon atoms; an aryl group of 6 to 30 carbon atoms; a heterocyclic group of 3 to 30 carbon atoms; or a functional group represented by the following Formula 1a or Formula 1b, and n is an integer of 1 to 5, and at least one of $R_5$ groups is a functional group represented by the following Formula 1a or Formula 1b, in case where n is an integer of 2 to 5, a plurality of $R_5$ groups may be the same or different,

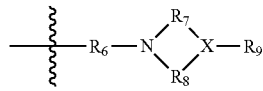

[Formula 1a]

in Formula 1a, $R_6$ is a substituted or unsubstituted alkylene group of 1 to 20 carbon atoms with a substituent; a substituted or unsubstituted cycloalkylene group of 5 to 20 carbon atoms with a substituent; or a substituted or unsubstituted arylene group of 6 to 20 carbon atoms with a substituent, wherein the substituent is an alkyl group of 1 to 10 carbon atoms, a cycloalkyl group of 5 to 10 carbon atoms, or an aryl group of 6 to 20 carbon atoms, $R_7$ and $R_8$ are each independently a substituted or unsubstituted alkylene group of 1 to 20 carbon atoms with an alkyl group of 1 to 10 carbon atoms, a cycloalkyl group of 5 to 10 carbon atoms, or an aryl group of 6 to 20 carbon atoms, $R_9$ is hydrogen; an alkyl group of 1 to 30 carbon atoms, an alkenyl group of 2 to 30 carbon atoms; an alkynyl group of 2 to 30 carbon atoms; a heteroalkyl group of 1 to 30 carbon atoms; a heteroalkenyl group of 2 to 30 carbon atoms; a heteroalkynyl group of 2 to 30 carbon atoms; a cycloalkyl group of 5 to 30 carbon atoms; an aryl group of 6 to 30 carbon atoms; or a heterocyclic group of 3 to 30 carbon atoms, and X is an N, O or S atom, in case where X is O or S, $R_9$ is not present,

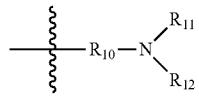

[Formula 1b]

in Formula 1b, $R_{10}$ is a substituted or unsubstituted alkylene group of 1 to 20 carbon atoms with a substituent; a substituted or unsubstituted cycloalkylene group of 5 to 20 carbon atoms with a substituent; or a substituted or unsubstituted arylene group of 6 to 20 carbon atoms with a substituent, wherein the substituent is an alkyl group of 1 to 10 carbon atoms, a cycloalkyl group of 5 to 10 carbon atoms, or an aryl group of 6 to 20 carbon atoms, and $R_{11}$ and $R_{12}$ are each independently an alkyl group of 1 to 30 carbon atoms; an alkenyl group of 2 to 30 carbon atoms; an alkynyl group of 2 to 30 carbon atoms; a heteroalkyl group of 1 to 30 carbon atoms; a heteroalkenyl group of 2 to 30 carbon atoms; a heteroalkynyl group of 2 to 30 carbon atoms; a cycloalkyl group of 5 to 30 carbon atoms; an aryl group of 6 to 30 carbon atoms; or a heterocyclic group of 3 to 30 carbon atoms,

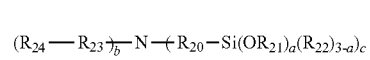

[Formula 2]

in Formula 2, $R_{20}$ is a single bond, or an alkylene group of 1 to 10 carbon atoms, $R_{21}$ and $R_{22}$ are each independently an alkyl group of 1 to 10 carbon atoms, $R_{23}$ is a single bond or an alkylene group of 1 to 10 carbon atoms, $R_{24}$ is hydrogen, an alkyl group of 1 to 10 carbon atoms or a substituted divalent, trivalent or tetravalent alkylsilyl group with an alkyl group of 1 to 10 carbon atoms, a is an integer of 2 or 3, c is an integer of 1 to 3, and b is an integer of 0 to 2, where b+c=3,

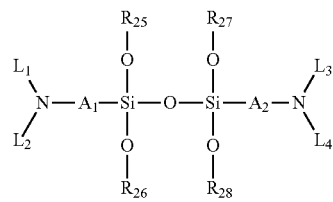

[Formula 3]

in Formula 3, $A_1$ and $A_2$ are each independently an alkylene group of 1 to 20 carbon atoms, $R_{25}$ to $R_{28}$ are each independently an alkyl group of 1 to 20 carbon atoms, and $L_1$ to $L_4$ are each independently a substituted divalent, trivalent or tetravalent alkylsilyl group with an alkyl group of 1 to 10 carbon atoms, or an alkyl group of 1 to 20 carbon atoms, wherein the modified conjugated diene-based polymer having a unimodal molecular weight distribution, and a polydispersity index of 1.0 to less than 1.7.

2. The modified conjugated diene-based polymer according to claim 1, wherein in Formula 1, $R_1$ to $R_3$ are each independently hydrogen; an alkyl group of 1 to 10 carbon atoms, an alkenyl group of 2 to 10 carbon atoms, or an alkynyl group of 2 to 10 carbon atoms, $R_4$ is a single bond; an unsubstituted alkylene group of 1 to 10 carbon atoms, and $R_5$ is an alkyl group of 1 to 10 carbon atoms; an alkenyl group of 2 to 10 carbon atoms; an alkynyl group of 2 to 10 carbon atoms; or a functional group represented by Formula 1a or Formula 1b, in Formula 1a, $R_6$ is an unsubstituted alkylene group of 1 to 10 carbon atoms, $R_7$ and $R_8$ are each independently an unsubstituted alkylene group of 1 to 10 carbon atoms, and $R_9$ is an alkyl group of 1 to 10 carbon atoms; a cycloalkyl group of 5 to 20 carbon atoms; an aryl group of 6 to 20 carbon atoms; or a heterocyclic group of 3 to 20 carbon atoms, and in Formula 1b, $R_{10}$ is an unsubstituted alkylene group of 1 to 10 carbon atoms, and $R_{11}$ and $R_{12}$ are each independently an alkyl group of 1 to 10 carbon atoms; a cycloalkyl group of 5 to 20 carbon atoms; an aryl group of 6 to 20 carbon atoms; or a heterocyclic group of 3 to 20 carbon atoms.

3. The modified conjugated diene-based polymer according to claim 1, wherein
in Formula 2,
$R_{20}$ is a single bond, or an alkylene group of 1 to 5 carbon atoms,
$R_{21}$ and $R_{22}$ are each independently an alkyl group of 1 to 5 carbon atoms,
$R_{23}$ is a single bond or an alkylene group of 1 to 5 carbon atoms, and
$R_{24}$ is hydrogen, an alkyl group of 1 to 5 carbon atoms or a substituted tetravalent alkylsilyl group with an alkyl group of 1 to 5 carbon atoms.

4. The modified conjugated diene-based polymer according to claim 1, wherein
in Formula 3,
$A_1$ and $A_2$ are each independently an alkylene group of 1 to 10 carbon atoms,
$R_{25}$ to $R_{28}$ are each independently an alkyl group of 1 to 10 carbon atoms, and
$L_1$ to $L_4$ are each independently a substituted tetravalent alkylsilyl group with an alkyl group of 1 to 5 carbon atoms, or an alkyl group of 1 to 10 carbon atoms.

5. The modified conjugated diene-based polymer according to claim 1, wherein the modified conjugated diene-based polymer has a number average molecular weight (Mn) of 1,000 g/mol to 2,000,000 g/mol, and a weight average molecular weight (Mw) of 1,000 g/mol to 3,000,000 g/mol.

6. The modified conjugated diene-based polymer according to claim 1, wherein the modified conjugated diene-based polymer has a Si content of 50 ppm or more and a N content of 50 ppm or more, respectively, based on the total weight of the modified conjugated diene-based polymer.

7. The modified conjugated diene-based polymer according to claim 1, wherein the modified conjugated diene-based polymer has a mooney stress relaxation ratio of 0.7 to 3.0 when measured at 100° C.

8. The modified conjugated diene-based polymer according to claim 1, wherein the modified conjugated diene-based polymer has a shrinking factor of 1.0 to 3.0, the shrinking factor being an average value of a ratio ($[\eta]/[\eta]_0$) of intrinsic viscosity ($[\eta]$) of the polymer at an absolute molecular weight to the intrinsic viscosity ($[\eta]_0$) of a linear polymer at the absolute molecular weight.

9. The modified conjugated diene-based polymer according to claim 1, wherein the modified conjugated diene-based polymer has a coupling number (C.N.) of 1<C.N.<F, where F is a number of functional groups of the modifier.

10. A rubber composition comprising the modified conjugated diene-based polymer of claim 1 and a filler.

11. The rubber composition according to claim 10, wherein the rubber composition comprises 0.1 parts by weight to 200 parts by weight of the filler based on 100 parts by weight of the modified conjugated diene-based polymer.

12. The rubber composition according to claim 10, wherein the rubber composition comprises 20 to 60 parts by weight of a process oil based on 100 parts by weight of the modified conjugated diene-based polymer.

* * * * *